United States Patent
Echols

(10) Patent No.: US 11,730,831 B2
(45) Date of Patent: Aug. 22, 2023

(54) IMAGING AGENTS AND METHODS OF USING THE SAME

(71) Applicant: SICreations, LLC, Salt Lake City, UT (US)

(72) Inventor: Michael Scott Echols, Salt Lake City, UT (US)

(73) Assignee: SICREATIONS, LLC, Salt Lake City, UT (US)

( * ) Notice: Subject to any disclaimer, the term of this patent is extended or adjusted under 35 U.S.C. 154(b) by 408 days.

(21) Appl. No.: 16/831,688

(22) Filed: Mar. 26, 2020

(65) Prior Publication Data

US 2020/0323998 A1    Oct. 15, 2020

Related U.S. Application Data

(60) Provisional application No. 62/824,051, filed on Mar. 26, 2019.

(51) Int. Cl.

| | | |
|---|---|---|
| *A61K 49/04* | (2006.01) | |
| *A61K 47/46* | (2006.01) | |
| *A61K 47/18* | (2017.01) | |
| *A61K 47/10* | (2017.01) | |
| *A61K 31/137* | (2006.01) | |
| *A61M 5/00* | (2006.01) | |
| *A61B 6/00* | (2006.01) | |
| *A61K 31/439* | (2006.01) | |

(52) U.S. Cl.
CPC .......... *A61K 49/0438* (2013.01); *A61B 6/481* (2013.01); *A61B 6/503* (2013.01); *A61B 6/504* (2013.01); *A61K 31/137* (2013.01); *A61K 31/439* (2013.01); *A61K 47/10* (2013.01); *A61K 47/18* (2013.01); *A61K 47/46* (2013.01); *A61M 5/007* (2013.01); *A61M 2205/32* (2013.01)

(58) Field of Classification Search
CPC .... A61K 49/0438; A61K 6/481; A61K 6/503; A61K 6/504; A61K 31/137; A61K 31/439; A61K 47/10; A61K 47/18; A61K 47/46; A61K 49/0409; A61K 49/0447; A61K 45/06; A61M 5/007; A61M 2205/32; A61B 6/032; A61B 6/507; A61B 6/508; A61B 6/5247

See application file for complete search history.

(56) References Cited

U.S. PATENT DOCUMENTS

| | | |
|---|---|---|
| 6,246,901 B1 | 6/2001 | Benaron |
| 2004/0052728 A1 | 3/2004 | Eriksen et al. |
| 2004/0241093 A1 | 12/2004 | Lauenstein et al. |
| 2008/0003561 A1 | 1/2008 | Woods et al. |
| 2010/0166664 A1 | 7/2010 | Butts et al. |
| 2011/0243847 A1 | 10/2011 | Wiebelitz |
| 2016/0030601 A1 | 2/2016 | Echols |

FOREIGN PATENT DOCUMENTS

WO    WO-2016054658 A1 *  4/2016  .......... A61K 31/167

OTHER PUBLICATIONS

International Search Report and Written Opinion of the International Searching Authority for application No. PCT/US2020/25072, dated Jun. 18, 2020.
International Search Report and Written Opinion of the International Searching Authority for application No. PCT/US2020/35346, dated Aug. 28, 2020.

* cited by examiner

*Primary Examiner* — Robert A Wax
*Assistant Examiner* — Quanglong N Truong
(74) *Attorney, Agent, or Firm* — Steptoe & Johnson LLP; Carl B. Wischhusen

(57) ABSTRACT

A composition for internal imaging of a subject includes an imaging contrast agent and one or more carrier agents that can pass through cellular and tissue membranes. Examples of imaging contrast agents are iodine-based, silver-based, or barium-based. Examples of carrier agents are dimethyl sulfoxide, urea, or an alcohol. Methods for internally imaging a subject using such a composition are also disclosed.

27 Claims, 25 Drawing Sheets

IMAGING AGENTS AND METHODS OF USING THE SAME

CLAIM OF PRIORITY

This application claims priority from U.S. Provisional Application No. 62/824,051, filed on Mar. 26, 2019, which is incorporated by reference in its entirety.

BACKGROUND

Embodiments of the present invention relate to the field of imaging and in particular to an improved composition and process for imaging an entire living or deceased organism.

The field of imaging (or visualization) runs from simple observation of treated subjects to advanced imaging using X-ray-based technology including Computed Tomography (CAT or CT scans), magnetic resonance imaging (MRI), ultrasound, or high-resolution photography. In radiographic imaging studies, a relatively opaque white appearance corresponds to dense materials or substances, compared with a relatively darker appearance of less dense materials.

"Radiodensity" or "radiopacity" refers to the relative inability of electromagnetic radiation, particularly X-rays, to pass through a particular material. "Radiolucency" indicates greater transparency or "transradiancy" to X-ray photons. Materials that inhibit the passage of electromagnetic radiation are called "radiodense," while materials that allow radiation to pass more freely are referred to as "radiolucent."

Contrast agents may be used to highlight specific structures to improve visualization of living and deceased organisms and non-biologic subjects. In the field of medicine, radiographic imaging has been revolutionized by radiodense contrast media, which can be passed through the bloodstream, the gastrointestinal tract, or into the cerebrospinal fluid (CSF). Radiodense contrast media may be used to highlight computed tomography (CT) scans or X-ray images and provide the ability to generate highly accurate and detailed anatomic and physiologic images of the body in a noninvasive manner.

Magnetic resonance imaging (MRI) uses magnetic fields and radio waves to generate images. While both CT and MRI differentiate tissue density, MRI more accurately differentiates proton (mostly hydrogen) densities. MRI also differentiates between tissue relaxation relative to magnetization. Because hydrogen protons are most predominant in water, soft tissue generates more "signal" than bone with MRI. The larger the MRI magnet (measured in teslas or "T"), the better the ability of the machine to distinguish between the biologic states of the atoms it is reading. This translates into better resolution of the final images. The magnet aligns the protons. Subsequently, the machine produces radiofrequency waves that vary the magnetic field and disrupts the protons' spins. The field is then turned off, and the protons return to their normal spin ("reorient") producing a radio signal that is measured by the detector. These data are then converted into an image. During a T1-weighted image or MRI, protons reorient resulting in recovery of longitudinal magnetization. T1 images show water (like CSF) as dark and fat (like white matter) as white. T1 images are good at demonstrating anatomy. During a T2-weighted image or MRI, protons reorient resulting in decay of transverse magnetization. In T2 images, water appears bright and fat appears dark. Because many diseases are associated with a change in water content, T2 images are better at showing pathology.

Ultrasound (or ultrasonography) provides real-time (immediate) information of a scan area and is readily available and typically lower cost than both CT and MRI. Ultrasound uses high frequency sound waves to delineate tissue structures. The ultrasound transducer converts electrical signals into ultrasound waves that are directed into a subject's tissues. The sound waves bounce off the subject's tissues and return to the transducer where the returned waves are converted back into electrical signals. A computer then converts the electrical signals into an image. Images represent the tissue's relative effect on the passing sound waves. Water-based tissues tend to be good transducers of sound waves while those with air, metal, bone, stones, and metal implants are poor transducers. Thus, dense (e.g., bone) and air-filled tissues tend to block the passage of ultrasound waves creating image voids or artifacts. Moreover, only a small area can be scanned at any given time High-resolution photography may also be used to visualize structures of a subject. Newer camera technology products are capable of resolutions of 10 microns or less. This technology is likely to improve over time. Subjects may be photographed externally or "thin-sliced" and photographed at each slice level. The photographs may be compiled (much like a CT or MRI) to create stacks of images that can then be studied three dimensionally creating exceptional studies that accurately depict the 3D structures of the subject. Although the method described (thin-slicing) is destructive, it does allow for a detailed accounting of the subject. Contrast agents can be added systemically or at each level of the subject "slice" to highlight specific or multiple structures. Additionally, before and after images of the unaltered and contrast-stained slice may be studied via subtraction and other methods to visually enhance or highlight specific structures (with and without "stain").

Each of these modalities has some benefits. Conventionally, CT is best (in terms of speed and resolution) for visualizing the skeletal system, whereas MRI offers unparalleled soft-tissue contrast (e.g., grey and white matter in the brain). Ultrasound best provides information on soft tissue structures and flow (doppler ultrasound) and usually as a 2D image (although 3D constructs are possible with newer technology). Newer digital camera technology offers true color image capture with incredible detail.

There are different types of materials that can be used as a contrast agent. Iodine and barium compounds are used as a contrast agent because of their high X-ray absorption. Dimethyl sulfoxide (DMSO) and alcohol may be used as contrast agents. Resins, such as methyl methacrylate-based compounds, may also be used as contrast agents. A resin fills a subject's vasculature and then polymerizes. After polymerization, the tissue can be dissolved, thin-sliced, or otherwise modified, and a fragile construct forms that can be imaged. A drawback is that filling the vasculature with a resin takes a long time.

By using either exogenous or endogenous contrast agents, additional information of the body can be captured. For example, images of the vascular system (i.e., angiography) can be obtained via contrast-enhanced digital subtraction CT or time-of-flight MRI. The detailed, morphological analysis of the vascular tree allows for assessing the basic anatomy, physiological conditions, and metabolic functions of the subject.

Several contrast agents are commonly used with MRI. Most contrast agents, such as gadolinium-based compounds, work by shortening the T1 relaxation time of protons, which in turn enhances the signal. The contrast agents are typically used on live animals but can be used to study deceased animals. Most contrast agents are delivered via intravenous (IV) or intrathecal routes. Some contrast agents can be administered orally for gastrointestinal MRI studies. Because gadolinium chelates are hydrophilic and do not cross the blood-brain barrier, these compounds can be useful with tumors and other lesions that break down this barrier. The gadolinium essentially leaks out of the vasculature defining the abnormal tissue. OMNISCAN® (gadodiamide, GE HealthCare) and PROHANCE® (gadoteridol, Bracco Imaging) are examples of available gadolinium-based MRI contrast agents. Because prepared BRITEVU® (barium based, Scarlet Imaging, LLC) solution is composed primarily of water (source of hydrogen protons), this contrast agent provides excellent MRI contrast for terminal studies. Additionally, gadolinium can be added to the BRITEVU® solution for additional MRI contrast. Other contrast agents, like iron-containing compounds, affect T2 relaxation for MRI studies. Other metal chelates are available that target specific tissues or cells and may be used as MRI or CT contrast agents.

There are also several contrast agents that are used with ultrasound. By simply filling collapsed vessels with fluid, gel, and other semisolid compounds, ultrasound images may be improved. Microbubbles contrast agents (such as sulphur hexafluoride microbubbles (SONOVUE®, Bracco Imaging), octafluoropropane gas core with an albumin shell (OPTISON, GE Healthcare) and air within a lipid/galactose shell (LEVOVIST, Schering AG) improve the image or other information gained during an ultrasound study. Many of the microbubble products have been shown to be safe for use in live subjects. Fabrizio Calliada et al., *Ultrasound Contrast Agents: Basic Principles*, 27 Eur. J. Radiology, Suppl 2:S157-60 (May 1998). Water-based terminal contrast agents (such as BRITEVU®) that fill the vasculature can also improve ultrasound imaging.

Regarding photography, many contrast agents can be used to spot or systemically "stain" or paint tissue to enhance certain structures. For example, fluorescein dye can be added to vascular-delivered (CT, MRI, and ultrasound) contrast agents to better highlight the vascular system using standard (e.g., incandescent) and UV light. In another example, many iodine-based compounds stain different tissues a differential brown hue that be can be used to highlight specific structures. In another example, silver-based stains tend to impart a grey-blue to black hue to stained nervous tissue depending on the specific nerve type. All are examples of how tissue stains can be used to enhance photographic images.

Contrast imaging began as early as the 1920s with the use of barium swallows visualized with X-ray technology, and since then many forms of contrast agents have been developed and used in medicine, research, the arts, and other applications. Forms of contrast agents have been practiced on biologic (both live and dead) and non-biologic specimens. Today, contrast-based studies are commonplace in clinical and research-based applications. In 2015, Beckett et al. reported "half of the approximately 76 million computed tomographic (CT) and 34 million magnetic resonance imaging (MRI) examinations performed each year include the use of intravenous contrast agents." Katrina R. Beckett et al., *Safe Use of Contrast Media: What the Radiologist Needs to Know*, 35 RadioGraphics 1738-1750 (October 2015).

Contrast agents work by enhancing subject matter visualization. For example, iodinated and other compounds (sodium, bismuth, potassium and lithium iodide, Lugol's iodine, clinical iodine-based compounds, barium-based products, gold nanoparticles, and others) increase the X-ray attenuation of tissues that take up (diffusible) or are in contact with (perfusible) the contrast agent. By increasing relative density, contrast agents help make the target tissue/subject more visible using X-ray technology such as CT scanning. MRI contrast agents work by shortening or increasing the T1 or T2 relaxation time of exposed tissues. Relative differences in the T1 relaxation time of water protons in different tissues primarily provides contrast seen in magnetic resonance (MR) images. Gadolinium-based contrast agents affect T1 relaxation time. T2 relaxation times also affect MR images and can be altered by iron and other materials contained or used in contrast agents. As above, vascular and tissue filling agents and microbubble intravascular agents can improve ultrasound studies.

Traditionally, contrast agents used with advanced imaging have been divided into diffusible and perfusible categories. Diffusible contrast agents are those that diffuse across membranes. The subject to be imaged is often soaked in a solution containing a diffusible agent illustratively including Lugol's iodine. Some agents such as hexamethyldisilazane can be combined with drying agents, such as alcohols, to increase tissue contrast when viewed with X-rays. Diffusible agents diffuse at specific rates and often must be replenished until the subject is adequately contrast stained (as determined by advanced imaging). The subject can be living, dead, biologic, and non-biologic. The size of the subject is often the rate-limiting consideration as diffusible contrast agents can only diffuse small areas (often on the level of mm or cm in depth). As noted by Gignac et al., "specimens should be fixed thoroughly prior to staining and imaging." Paul M. Gignac et al., Diffusible Iodine-Based Contrast-Enhanced Computed Tomography (diceCT): An Emerging Tool for Rapid, High-Resolution, 3-D Imaging of Metazoan Soft Tissues, 228 J. Anatomy 889-909 (June 2016). Fixation prior to contrast diffusion prevents degradation of the tissue while waiting for complete penetration of the diffusion agent. However, an entire diffusion process can take days or weeks to months. Furthermore, fixation protocols can distort tissue by cross-linking proteins, reducing water content, and other changes. These distortions may ultimately result in altered anatomy of the subject even if the subject is not physically handled or further manipulated.

Diffusible agents can contrast stain (or enhance) multiple tissue types present in a penetration zone and allow for differential "staining." When viewed using advanced imaging, differential staining translates into varying degrees of contrast uptake. The end result is that tissues with different contrast amounts appear visually distinct from one another especially when viewed with advanced imaging (CT, MRI, etc.). The differential staining allows viewers to identify specific tissues, portions of tissues, and even different cells when using micro-imaging techniques as with some micro-CT and nano-CT studies.

Among the challenges of using diffusible agents is getting different tissue types (including down to cell level) to not only stain (take up contrast) differentially, but also evenly diffuse throughout the tissue being stained. Uneven distribution of the contrast stain tends to result in some areas (most often those in first contact with the agent) to overstain (which may be represented as excess radiodensity or T1/T2 relaxation on a CT scan or MRI, respectively). Likewise, those tissues furthest from the closest point of contact with the contrast stain may be understained (which may be represented as low radiodensity on CT or minimal effect on T1/T2 relaxation times). One partial solution to uneven uptake of diffusible agents is to administer the diffusible agents via a route that more evenly exposes the test subject.

An example of this is using diffusible agents like a perfusible product by injecting the stain into the vascular system. This process more evenly exposes the test subject. However, it does not address the overstaining issue as the tissues of first contact are still at risk of taking on too much contrast agent and artificially representing contrast stain uptake.

Perfusible (or perfusion-based) contrast agents are delivered into a system (such as the circulatory, respiratory, or lymphatic system) and do not cross the barrier of the system (assuming there is no functional break in a membrane, etc.). Perfusible contrast agents can be applied to living, dead, biologic, and non-biologic systems. Examples of perfusible agents include barium swallows for gastrointestinal contrast studies and iodinated compounds delivered intravenously for arteriovenograms. Perfusion-based agents are generally rapidly administered and define the shape and course only of the system being perfused when viewed with various imaging modalities. Often, perfusible agents never leave the perfused system (unless a rupture is present) and are ultimately eliminated from the subject. Some perfusible agents replace the normal volume of fluid and are permanent, such as terminal vascular casting agents. Perfusible agents are commonly used for both CT and MRI contrast studies. However, perfusible contrast agents may be used in other imaging modalities such as microbubbles and simple fluid volume loading used in ultrasound as described by Calliada et al.

Examples of CT-perfusible contrast agents include iohexol (OMNIPAQUE®, GE Healthcare); iopromide (ULTRAVIST®, Bayer Healthcare); iodixanol (VISIPAQUE®, GE Healthcare); ioxaglate (HEXABRIX®, Mallinckrodt Imaging); iothalamate (CYSTO-CONRAY® II, Mallinckrodt Imaging); iopamidol (ISOVUE®, Bracco Imaging); and diatrizoate (Renagrafin-76, Bracco Imaging). See Hrvoje Lusic and Mark W. Grinstaff, X-Ray-Computed Tomography Contrast Agents, 113 Chem. Rev. 1313-1350 (March 2013).

Lanthanide-based contrast agents are used primarily with MRI contrast imaging, but are sometimes also used with CT testing. Examples of lanthanide-based contrast agents used with CT and/or MRI testing include gadoversetamide (OPTIMARK®, Mallinckrodt Imaging), gadopentetate dimeglumine (MAGNEVIST®, Bayer Healthcare), gadobutrol (GADOVIST, Bayer Healthcare), gadobenate dimeglumine (MULTIHANCE®, Bracco Imaging), gadoterate meglumine (DOTAREM®, Guerbet), and gadoxetate disodium (EOVIST®, Bayer Healthcare). See Lusic and Grinstaff, supra. Terminal perfusible contrast agents (such as BRITEVU®) are often used to fill the internal structure of a system (respiratory, circulatory, etc.).

Other products have also been used as contrast agents to create special images (CT, MRI, ultrasound, etc.), see Lusic and Grinstaff, illustratively including gas bubbles, bismuth, silver, gold, iron, platinum, lead, rare-earth-based elements, nano-particles, and entrapped, conjugated, labeled, coated, or otherwise connected monoclonal antibodies, tissue receptors (for example, gastrin, folic acid, vitamin D), lipoproteins (high density lipoproteins, low density lipoproteins, etc.), cell specific (kidney, liver, etc.), tantalum, and high-Z noble gases (Xenon, etc.).

While perfusible contrast agents define the intact system into which the contrast agents are perfused, perfusible contrast agents do not generally contrast stain other tissues. In some cases, components of the perfused subject may selectively take up the stain and store it temporarily to permanently. For example, liver cells may selectively take up components of a systemic stain which would then highlight the target organ (liver in this example) and less so the entire subject. Still, all the diverse tissues/components of the subject are not differentially stained.

X-ray technology generally defines five basic density types: air, fat, soft tissue, bone, and metal. While CT generates composite X-ray (3-dimensional) images, the same five basic density types are seen. Software modification can improve some subtle variations in tissue density. However, resolution and differentiation of different soft tissue types is generally poor with CT.

MRI uses a different set of tissue differentiation principles including magnetic characteristics of tissues, movement of fluids (such as blood), and spectroscopic effects related to molecular structure. In terms of biologic tissues, variations in soft tissue structure are better defined with MRI compared with CT. However, MRI is generally deficient at providing information on those tissues that are poor in hydrogen, such as bone and many manufactured products (metal, plastic, etc.).

Photography offers tremendous variation in how a true image is "seen" by the camera or transmitted to film or digitally. For example, filtering (ultra-violet (UV), thermal, infrared, etc.) can alter the appearance of the image (and can be further enhanced by the addition of secondary agents such as contrast, fluorescein, cooling, heating, and other agents) as seen by the camera. Post-processing software can then further alter the image to highlight specific structures, colors, wavelengths, etc.

The main advantages of CT, X-ray, and photography technology are that these modalities are generally more available, less costly, more rapidly acquire images, and produce more detailed images compared to MRI. The advantages of MRI are the lack of radiation exposure (also true with photography and ultrasound) and increased soft tissue resolution compared to CT. Ultrasound also lacks radiation exposure and provides for good soft tissue resolution (primarily) in one tissue plane with each pass of the transducer.

Figure 1A:
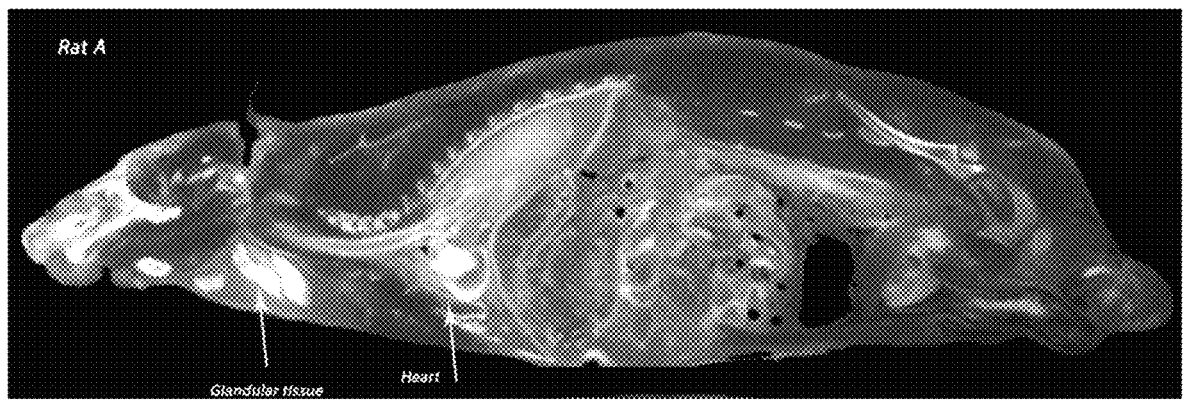
FIGS. 1A and 1B are images of two male rats perfused with a contrast stain and carrier agent, in accordance with embodiments of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

While there are many intravenous contrast agents, there is still a need for a contrast agent that can improve the image quality of a vascular and skeletal system of an entire animal.

The present invention is an intravenously, immersibly, or topically delivered imaging composition that can be used to image soft and/or hard tissue components of a subject using diffusible and perfusible contrast agents capable of differentially staining an entire subject and the subject's various component/tissue types, as well as corresponding structures of plants. Inventive embodiments of the imaging composition add carrier agents to diffusible and perfusible contrast agents. The use of a carrier agent promotes delivery of the contrast agent.

Embodiments of the invention use tissue/object staining properties of radiodense or other contrast agents combined with at least one carrier agent, with or without the addition of other enhancing agents that improve the penetration of the stain into the subject material. Embodiments of the intravenous composition may be used to perfuse whole subject systems to affect the entire subject, creating a density-staining process that can be completed in minutes to hours to days, compared to weeks or months previously. The whole subject perfusion results in rapid distribution of the stain providing differential contrast that is even, changes over time, and can be visualized using advanced imaging techniques such as X-ray, CT, photography, MRI, and/or ultrasound.

Contrast agents are used to highlight specific structures to improve visualization. The fields of visualization include those made with simple observation up to advanced imaging such as with X-ray based technology illustratively including computed tomography (CAT or CT scans), magnetic resonance imaging (MRI), advanced photography, and ultrasound.

Embodiments of the inventive imaging composition differentiate between organ systems (cardiovascular, lymphatic, musculoskeletal, integumentary, nervous, sensory organs (eyes, tongue, ears, nose), etc.) as well as between cell layers, regions, and tissue layers (e.g., arteries, veins, layers of intestine) within an organ system itself. The composition also differentiates between tissue types within cancerous and other abnormal tissues. It is noted that staining intensity and subject "tissue" differentiation changes with time. As the stain diffuses into the tissue, the staining intensity changes over time. This change in intensity can be easily noted within the first 24 hours of perfusion. This feature allows users to concentrate on different tissues at different time points to achieve ideal tissue intensity characteristics that are neither over nor under saturated. The present invention addresses prior art difficulties as to uniformity of staining and length of time to image a subject, which could run weeks or months.

Carrier agents can singly, or in combination with other compounds, pass through cellular and tissue membranes. Carrier agents are used in the pharmaceutical industry to transport drugs through membranes that are otherwise impermeable. They may also be used to deliver products through skin and other tissues. Carrier agents according to the present invention are used on biologic and non-biologic subjects. Carrier agents operative herein include DMSO (dimethyl sulfoxide), urea, and alcohol (e.g., ethanol and isopropyl alcohol), as well as 1-dodecylazacycloheptan-2-one (Azone), which is used to deliver drugs via a percutaneous route. See Richard B. Stoughton, *Enhanced percutaneous penetration with 1-dodecylazacycloheptan-2-one,* 118 Arch. Dermatol. 474-77 (July 1982). Parhi et al. teach that "Numerous class[es] of novel compounds have been evaluated for penetration enhancement activity, including soft enhancement for percutaneous absorption (SEPA), for example, 2-N-nonyl-1,3-dioxolanes, N-acetyl[ ] prolinate esters (such as pentyl- and octyl-N-acetyl[ ] prolinate), alkyldiloxanes (e.g., 1-Alkyl-3-b-D glucopyranosyl-1,1,3,3-tetramethyl disiloxanes), transcarbam (such as 5-(dodecyloxycarbonyl) pentylammonium-5-(dodecyloxycarbonyl) pentylcarbamate), iminosulfurane (like N-hexyl,N-benzoyl-S,S-dimethylimino-sulfuranes), capsaicin derivatives (e.g., nonivamide), cinnamene compounds (such as cinnamic acid, cinnamaldehyde[,] etc[.]), terpenes (like clove and basil oil) and synerg[i]stic combination of penetration enhancers (SCOPE)." Rabinarayan Parhi et al., *Novel Penetration Enhancers for Skin Applications: A Review,* 9 Curr. Drug Delivery 219-30 (March 2012). Cell penetrating peptides have also been used as tissue carrier agents and are being studied for processes as complex as gene transfection. See Chanuk Jeong et al., *A Branched TAT Cell-penetrating Peptide as a Novel Delivery Carrier for the Efficient Gene Transfection,* 20 Biomaterials Res., Article 28 (September 2016). Other products such as chitosan nanoparticles (CS- TPP-NPs), dimethyl sulfoxide, and hyaluronic acid-transethosomes have all been shown to have potential as carrier/transporter/drug delivery agents. See Anissa Tazrart et al., *Skin Absorption of Actinides: Influence of Solvents or Chelates on Skin Penetration Ex Vivo*, 93 Intl J. Radiation Biology 607-616 (June 2017); Nursyafiqah Sahrum Ayumi et al., *Polymeric Nanoparticles for Topical Delivery of Alpha and Beta Arbutin: Preparation and Characterization.* 9 Drug Delivery and Translational Res. 482-496 (March 2018); Silvia Franzé et al., *Hyaluronan-decorated Liposomes as Drug Delivery Systems for Cutaneous Administration*, 535 Intl J. Pharm. 333-339 (January 2018). Various alcohols, urea, and more may also be used as carrier agents.

It is further noted that many chemicals have been used with carrier agents to provide effects at both the local level and the system level. Some chemicals are used for local effects such as deep penetrating skin products that treat dermatologic disorders (triamcinolone acetonide plus a carrier agent). Other chemicals can also be applied via the same route (skin) and may be used to treat systemic disorders (testosterone plus a carrier agent used for the treatment of female sexual dysfunction). See Mark R. Prausnitz and Robert Langer, Transdermal Drug Delivery, 26 Nature Biotechnology 1261-1268 (November 2008). A non-exhaustive list of drugs used in combination with carrier agents include acyclovir, insulin, human growth hormone, granisetron, influenza vaccine, heat labile enterotoxin of *E. coli* and much more. Some of these agents target nerve receptors in known (and some unknown) mechanisms and illustratively include products such as lidocaine, buprenorphine, fentanyl, and rotigotine. Id. These examples only serve to show the diversity of classes of agents (hormones, pain medications, antivirals, vaccines and more) that can be combined with carrier agents.

In certain inventive embodiments when enhancing agents such as those that affect receptors, on/off switches, etc. (nerves, hormones, binding proteins, etc.) are delivered to the site of action, new products, actions, and more can be generated (proteins, immune responses, open/close action potentials, nerve impulse initiation and signaling, etc.). Receptors may be found in organic and inorganic structures. By delivering some compounds (such as via carrier agents and better dispersion methods), there are opportunities to create a response, product, etc. that can be further acted upon by the addition of another product introduced into the system (via carrier agent, diffusion, perfusion, or other dispersion method). Embodiments of the inventive process may be "laddered" to create a multitude of responses that would not otherwise be possible without exposing the target tissue to these specific agents.

Examples of enhancing agents include vasodilators and vasoconstrictors, atropine, N-acetyl aspartate, choline, epinephrine, norepinephrine, opioids and their derivative compounds, creatine, myosin, cholinesterase compounds, anticholinesterase compounds, paralytic agents, perfluorocarbon-based oxygen carriers, lactate, beta blockers, antimicrobials, calcium channel blockers, antidepressants, acetylcholinesterase inhibitors, barbiturates, non-opioid narcotics, non-steroidal anti-inflammatory agents, enzymes and enzyme inhibitors, and cell specific markers.

Embodiments of the intravenous imaging composition that use diffusible and perfusible agents may be used with different vascular conditioning agents to improve the distribution of the contrast agent and tissue type being stained. For example, a water-soluble vascular conditioning agent such as Dodge METAFLOW pre-tissue contrast stain gives a different contrast stain profile compared with lipid stripping products such as Dodge PROFLOW.

Prior to perfusion with the embodiments of the contrast and carrier agents, the vascular system may be conditioned to improve perfusion. For example, agents may be water based (water plus Dodge METAFLOW or PROFLOW plus or minus RECTIFIANT, for example) that are used to break up blood clots, adjust for minerals in added water, and aid in removal of clots of deceased subjects. Other compounds illustratively including anticoagulants (heparin, warfarin, etc.) may be added premortem to aid in the removal blood and/or prevent blood clotting (which also aids in the removal of blood). Additionally, hypotonic to hypertonic agents may be used to rupture blood cellular components thereby improving the removal of blood. By removing blood clots, the vascular system becomes more "open" or penetrable by the contrast and carrier agents. Additionally, blood components may interact with certain contrast agents (such as silver-based compounds or barium based). It is best to remove as many blood components prior to perfusion as possible to reduce adverse reactions. This in turn results in better perfusion and more even diffusion across the vascular system and into target tissues.

In some inventive embodiments, additional agents used to reduce odors and/or act as chemical disinfectants and may also be added to the contrast solution that do not significantly detract from the contrast staining abilities. Odor-reducing agents may be added to reduce unpleasant smells that may be associated with the chemical composition by itself and/or reaction with the perfused subject's (biologic and/or non-biologic) makeup. These compounds may include natural and artificial scents and flavorings, disinfectants, antimicrobials, etc., such as vanilla extract, orange (or other citrus) extract, urea, and alcohol.

Embodiments of the invention use tissue/object staining properties of radiodense or other stains combined with one or more carrier agents with or without the addition of other enhancing agents that improve the penetration of the stain into the subject material and/or targets specific cells, tissues, structures, etc. Embodiments of the inventive process may be used as a whole or partial system perfusion to affect the entire subject creating a density staining process that can be completed in minutes to hours to days. The whole or partial subject perfusion can also result in rapid distribution of the stain providing differential contrast that is even, changes over time, and can be visualized using advanced imaging techniques such as X-ray, CT, MRI, photography, and/or ultrasound.

For animal subjects, including mammals, birds, amphibian, reptiles, fish, and invertebrates, embodiments of the inventive imaging agent may be injected into the vascular system, lymphatic system, respiratory system, or other potential spaces for local, regional, or whole-body perfusions. Alternatively, the subject (local, regional, or whole) may be soaked in the tissue stain solution. Alternatively, the solution may be injected (via a needle and syringe for example) into the subject for local, regional, or whole-body diffusion staining. The subject may also be subjected to increased or decreased pressure, as with a hyperbaric or other chamber, to increase or otherwise alter the rate of diffusion of perfused or direct contact staining agents.

For plant subjects, embodiments of the inventive imaging agent may be delivered by one of four main pathways. The first pathway is by direct uptake from the roots, which includes cleaning the roots and suspending the plant in the tissue stain solution or "watering" the plant (ideally residing within a container) with the tissue stain solution. In this scenario, the plant is left intact and takes up the tissue stain solution via contact with the root system. The second pathway is by uptake from cut plants. The plant portion (whether a leaf, bud, stem, flower, fruit, etc.) is cut from its main structure and placed in the tissue stain solution. In this scenario, the plant takes up the staining solution directly from the cut exposed portion. In the third pathway, the plant may be injected (using a needle and syringe for example) with the tissue stain solution for local, regional, or whole plant injection diffusion. In the fourth pathway, the plant may be directly soaked, sprayed, painted, etc. in/with the tissue stain solution for local, regional, or whole plant "topical" diffusion staining.

For fungus and non-biologic subjects, the same approaches as described for animals and plants may be used and modified as needed for the studied subject.

Embodiments of the invention demonstrate the use of a carrier agent in combination with contrast agents and other drugs in order to improve the ability of diffusible and perfusible agents to provide contrast within one or more tissue/components of a subject to be better visualized using simple (simple visualization, dissection, photography, etc.) to advanced imaging techniques (CT, MRI, ultrasound, etc.). The diffusible agents can be delivered throughout a subject like a perfusible agent. The diffusible agents can be combined with drugs, chemicals, and other substances and delivered topically or via direct contact to create local to systemic effects. Drugs, chemicals, and other substances can be delivered via a perfusion method with or without a diffusion product to affect different subject tissues/components in a therapeutic, diagnostic, investigative, or other manner. This procedure can be used on plants, animals, and non-biologic subjects.

In specific inventive embodiments, metallic compounds (such as silver nitrate) may be combined with a carrier agent, solubilizing, or permeabilizing agent (such as DMSO (dimethyl sulfoxide), urea, and/or alcohol) and perfused into the subject to highlight specific structures such as nerves. In one example, silver nitrate (2.5-50%) can be combined with a carrier agent (silver nitrate 2.5-90% to carrier agent v/v) and perfused into or applied to the subject. The combined product can be perfused into the cardiovascular system. Then carrier agent then carries the silver nitrate through the vascular system and into the target tissues. Due to the density of the metallic compound, the targeted tissue is then "visible" using X-ray technology such as with CT scanning.

Embodiments of the inventive imaging agent provide imaging to completely highlight the cardiovascular system using low-cost, relatively non-toxic, and easy-to-administer materials that can be readily viewed using CT or standard radiographs and produce high quality images. Embodiments of the composition provide imaging of completely perfused entire animal subject, rather than a portion as with prior art compositions, such as MICROFIL® (Flow Tech Inc.). As used herein, animal subject refers to a mammal, a reptile, an amphibian, fish, invertebrate, or an avian. Embodiments of the inventive composition flow through the subject vascular system without clogging vessels, arteries (arteriole and venule), and smaller capillaries. The CT slice thickness and resolution will determine the size of the vessels visualized. Scanning can begin immediately after perfusion with an embodiment of the invention is complete or perfused tissues can be harvested and stored in formalin, other preservatives or fixatives, cooled, etc. for later scanning. By adding dye to the carrier agent, visualization of small (and large) vessels and other tissues/components can be significantly improved during gross dissection.

Embodiments of the inventive composition allow for creation of gross and digital (with the aid of CT/radiography/MRI/photography/ultrasound) vessel or tissue visualization for anatomy study. Study may include classroom up to research study. "Study" includes anything where the anatomy of the study subject needs to be understood. Vascular anatomy knowledge gives one shape and size of organs, shunts and other vascular anomalies, tumors, and other tissues. Soft tissue, not just vascular, anatomy also serves to provide valuable information. This information is vital to understanding basic anatomy, biology, and behavior of tissues.

Subjects infused with embodiments of the inventive imaging composition may be used to create digital images that are used to help develop other imaging products and studies. For example, performing MRI time-of-flight on selected animals is conducted first, and then followed up with the contrast product injection and CT. The contrast CT images may be used as the gold standard to help in understanding what is being seen on the time-of-flight study (non-invasive means to look at blood vessels). In other words, a match between the two images (CT and MRI) can be made, and information from the contrast CT may be used to improve upon the MRI procedure. The same can be true with developing other imaging processes where an accurate vascular or tissue map (as created with embodiments of the inventive imaging agent) is needed for comparison.

EXAMPLES

Example 1

An embodiment of the inventive imaging agent is used with different vascular conditioning agents to improve the distribution of the contrast agent and tissue type being stained. In this example, a water-soluble vascular conditioning agent such as Dodge METAFLOW pre-tissue contrast stain gives a different contrast stain profile compared with lipid stripping products such as Dodge PROFLOW.

Figure 1B:
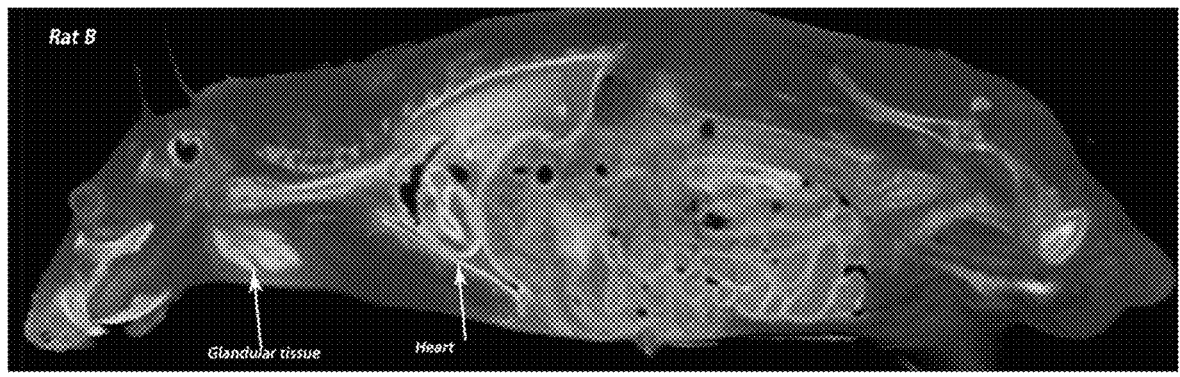

FIGS. 1A and 1B are images of two male rats perfused with the same concentration and dose of a contrast stain (radiodense, if using X-ray or CT) and carrier agent (e.g., DMSO) and then CT-scanned (at 200 μm resolution) two hours post-vascular injection where Rat A (FIG. 1A) was pre-flushed with a water-soluble vascular conditioning agent (Dodge METAFLOW) and Rat B (FIG. 1B) was pre-flushed with a lipid stripping vascular conditioning agent (Dodge PROFLOW) prior to perfusion with the contrast agent. Comparing FIG. 1A to FIG. 1B, Rat A has more intense and diffuse stain uptake (greater density) in the glandular tissue and heart muscle (ventricle) wall compared with Rat B. Rat A also demonstrates more intense stain uptake (greater density) in the bones. This example demonstrates how two different pre-flush preparations can have significant effects on the contrast stain uptake in various tissues given that all other variables are the same (contrast stain composition, dose, and delivery method, CT scanning parameters, time of CT after contrast stain perfusion) or very similar (two different rats of the same breed and approximately same size).

Example 2

Figure 2A:
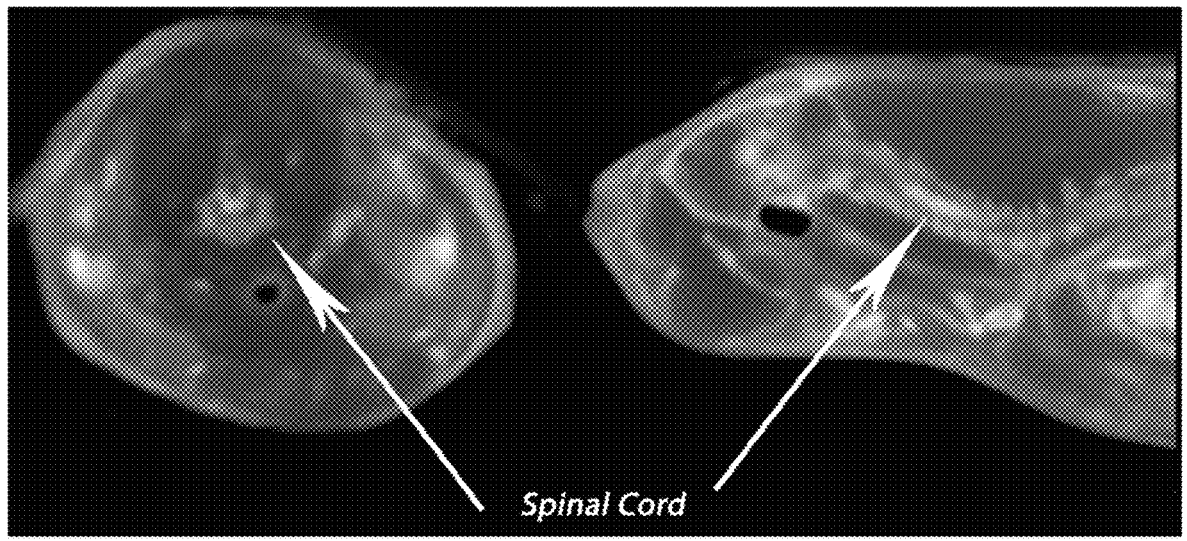
FIGS. 2A-2I illustrate using an imaging agent to differentiate types of neural tissue using iodine-based (FIGS. 2A-2G) and silver-based (FIGS. 2H-2I) contrast agent and a carrier agent in accordance with embodiments of the present invention.
Figure 2B:
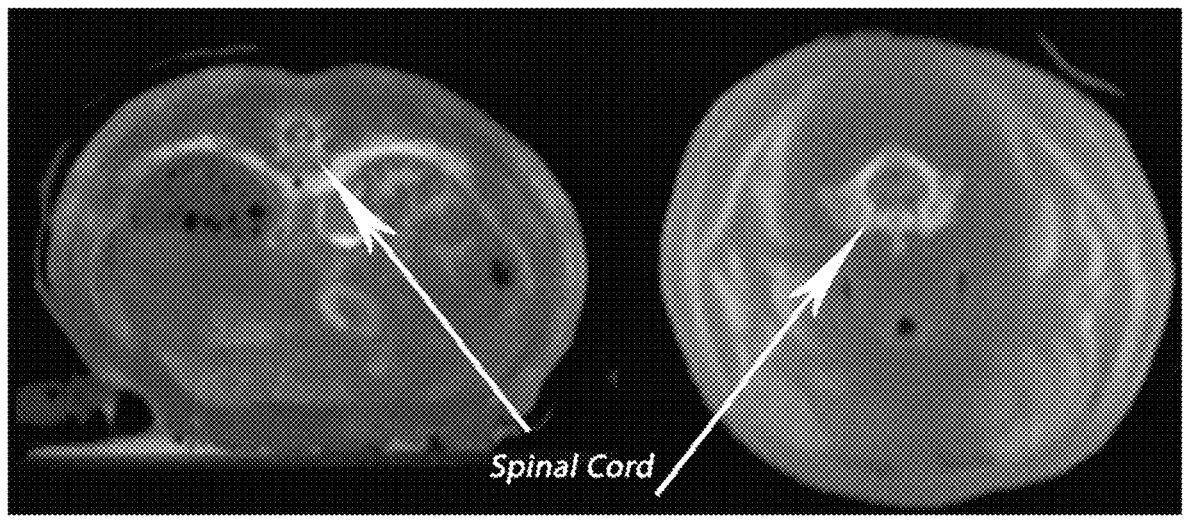
Figure 2C:
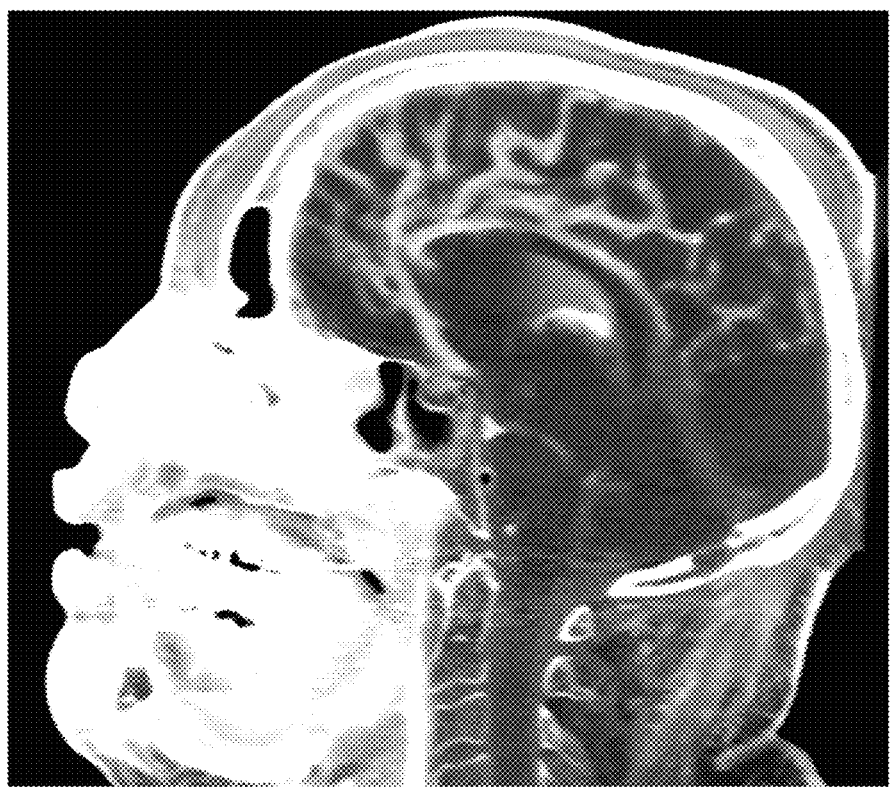
Figure 2D:
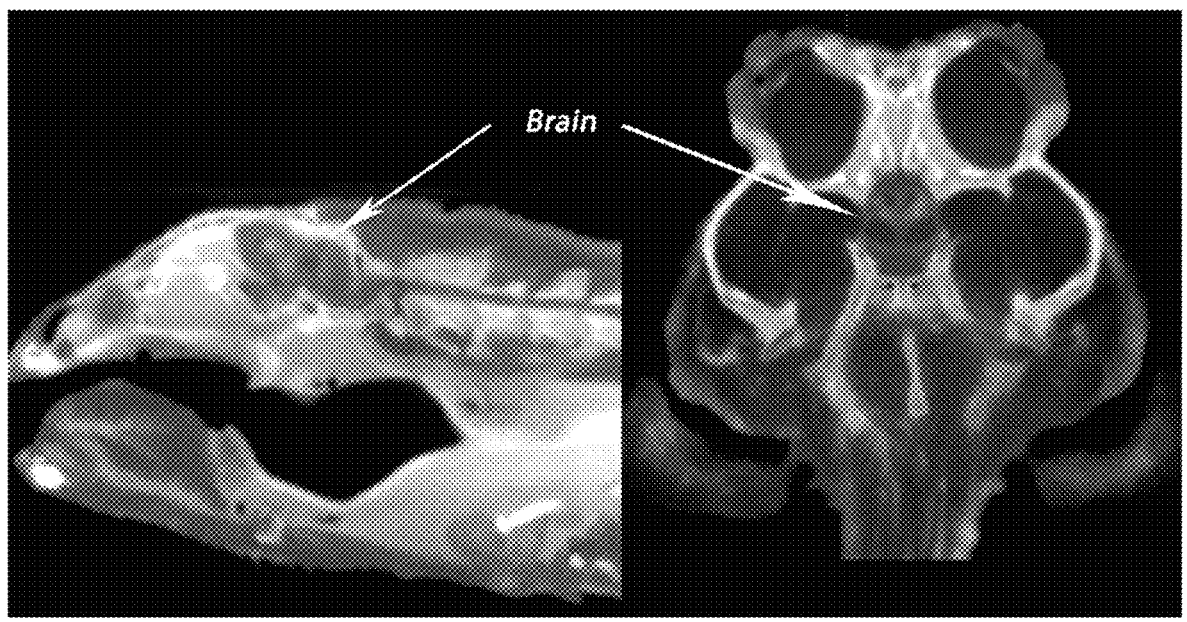

FIGS. 2A-2H illustrate using an imaging agent to differentiate types of neural tissue using iodine-based (FIGS. 2A-2G) and silver-based (FIGS. 2H-2J) contrast agent and a carrier agent in accordance with embodiments of the invention. The carrier agent may be one of the aforementioned carrier agents. FIG. 2A shows a heparinized rat perfused with an iodine-based contrast agent with carrier agents DMSO and ethanol and then CT-scanned immediately (left in FIG. 2A, transverse plane) and two hours post-perfusion (right in FIG. 2A, sagittal plane) at 200 µm resolution. The "butterfly" arrangement of the grey central spinal cord tissue (left) is readily evident on the transverse view. The same contrasted white (more stain uptake and "brighter" CT signal) versus grey (less stain uptake and contrast) is evident on the sagittal (right) view. FIG. 2B shows a rat perfused with an iodine-based contrast agent with carrier agent DMSO and then CT-scanned immediately (left in FIG. 2B, transverse plane) and 18 hours post-perfusion (right in FIG. 2B, transverse plane). Much like in FIG. 2A, the grey matter of the spinal cord has taken up more contrast stain (equating to more radiodense material) creating a "brighter" signal on the CT scan. FIG. 2C shows an 89-year-old, female human cadaver systemically perfused with an iodine-based stain with carrier agents DMSO, urea, and ethanol and two odor-reducing agents (vanilla extract, orange extract) one week after death and then CT-scanned one hour post-perfusion at 0.625 mm. The brain is differentially stained. FIG. 2D shows a heparinized bearded dragon perfused with an iodine-based contrast agent with carrier agent DMSO and then CT-scanned one hour and 18 hours post-perfusion at 200 µm resolution. Even on this small lizard weighing 0.6 kg and CT-scanned using a clinical (non-micro CT) scanner at 200 µm, the different components of the brain are differentially stained and readily visible.

Figure 2E:
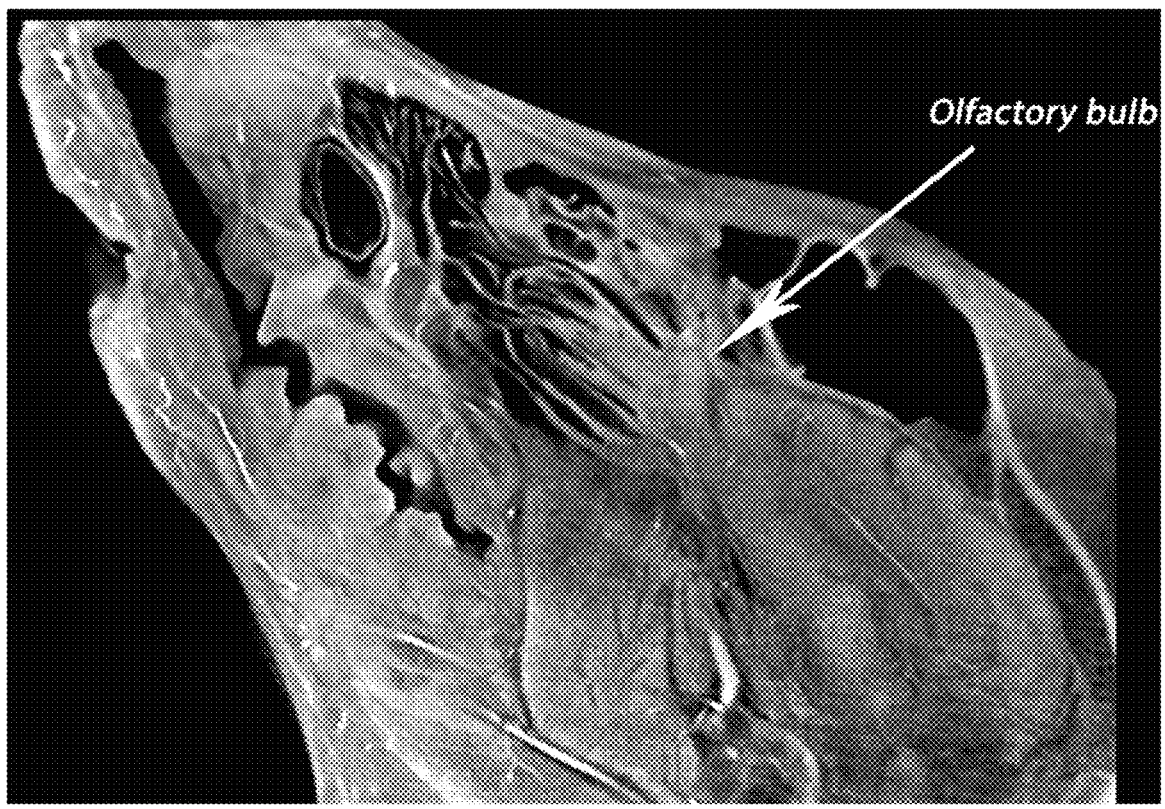
Figure 2F:
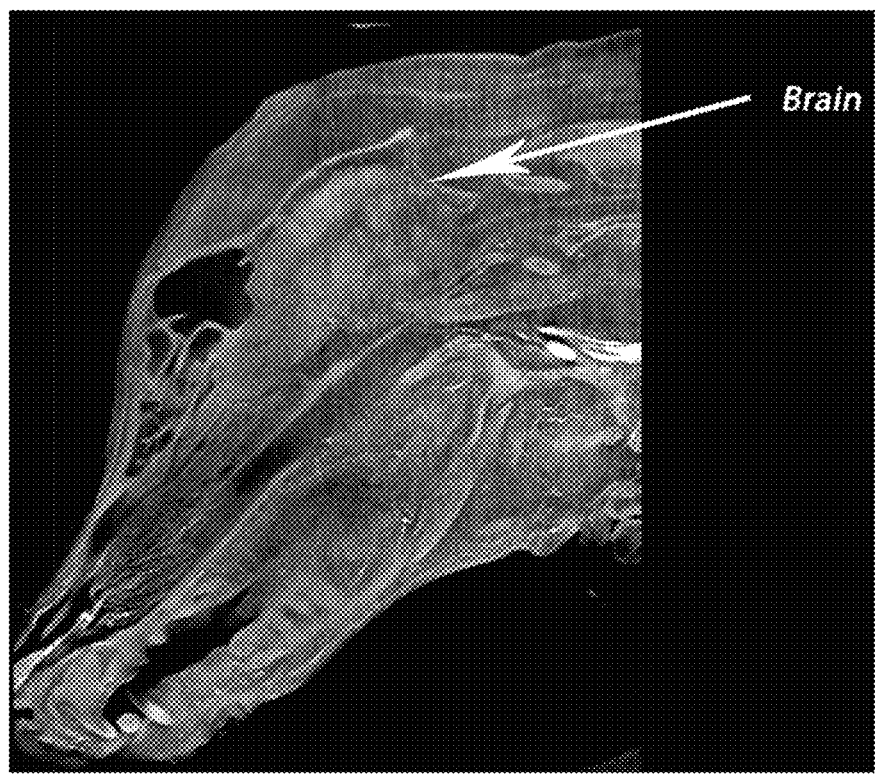

FIG. 2E shows a golden retriever perfused with an iodine-based contrast stain with a secondary contrast stain (e.g., a non-perfusible secondary contrast stain with barium sulfate), carrier agents urea, DMSO, and isopropyl alcohol, and two odor-reducing agents (vanilla extract, orange extract) and CT-scanned 26 hours later at 200 µm resolution. The olfactory bulb with its nerves penetrating through the cribriform plate are readily visible and distinguishable from the brain tissue immediately to the right. FIG. 2F shows the same golden retriever perfused with the same contrast stain, secondary contrast stain, carrier agents, and odor-reducing agents as in FIG. 2E and CT-scanned 26 hours later at 200 µm resolution. The brain is identified, and spinal cord contrast perfused. In this case, the white matter of the spinal cord is brighter (outer line) than the grey matter (central portion) which is opposite that seen in the examples shown in FIGS. 2A and 2B. This demonstrates how changes in the contrast makeup can effectively stain the same tissue type differently (even considering the different species that are compared here).

Figure 2G:
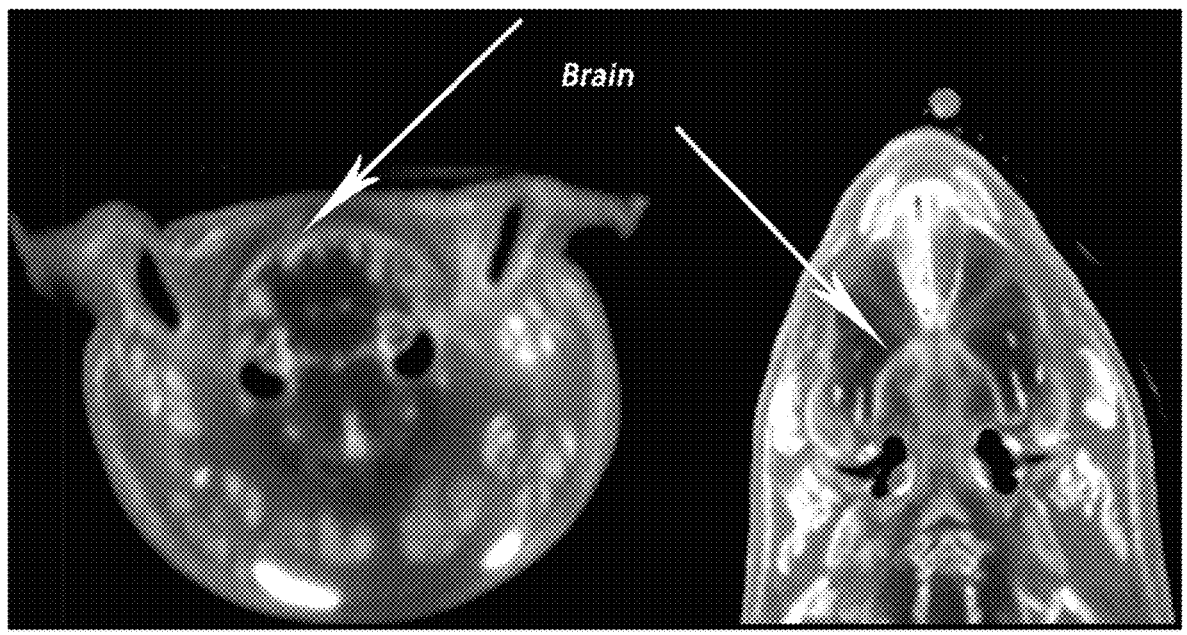
Figure 2H:
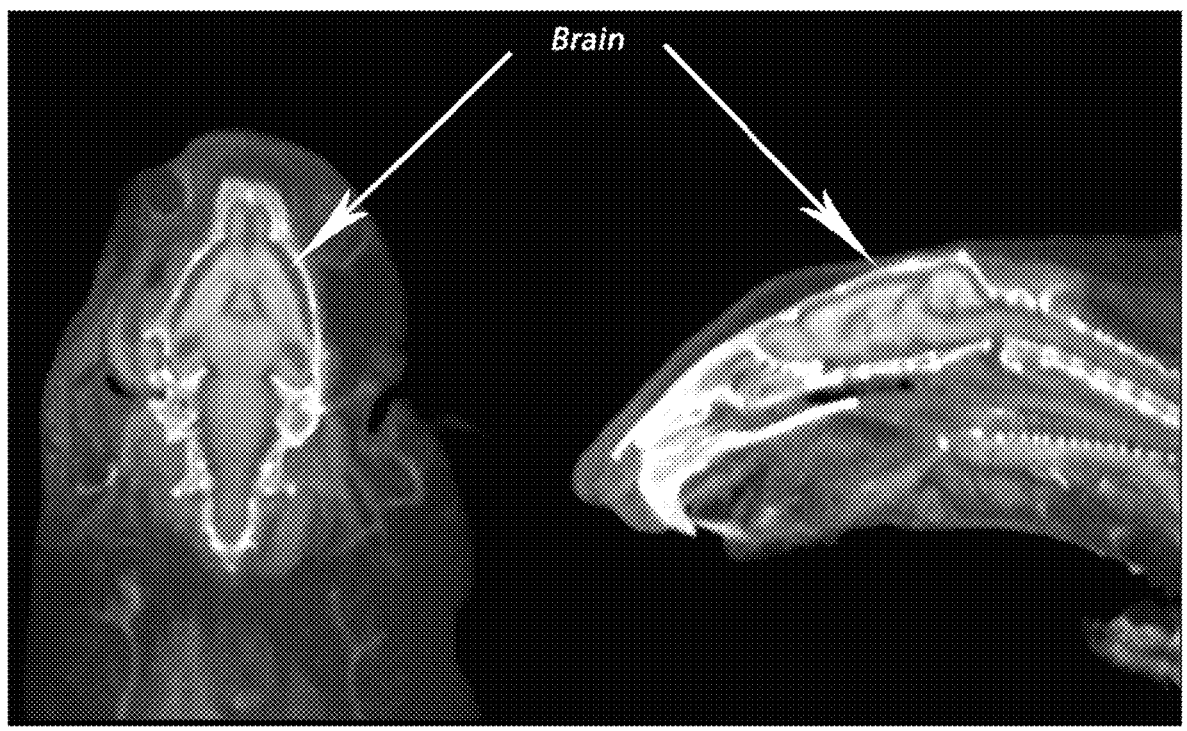
Figure 2I:
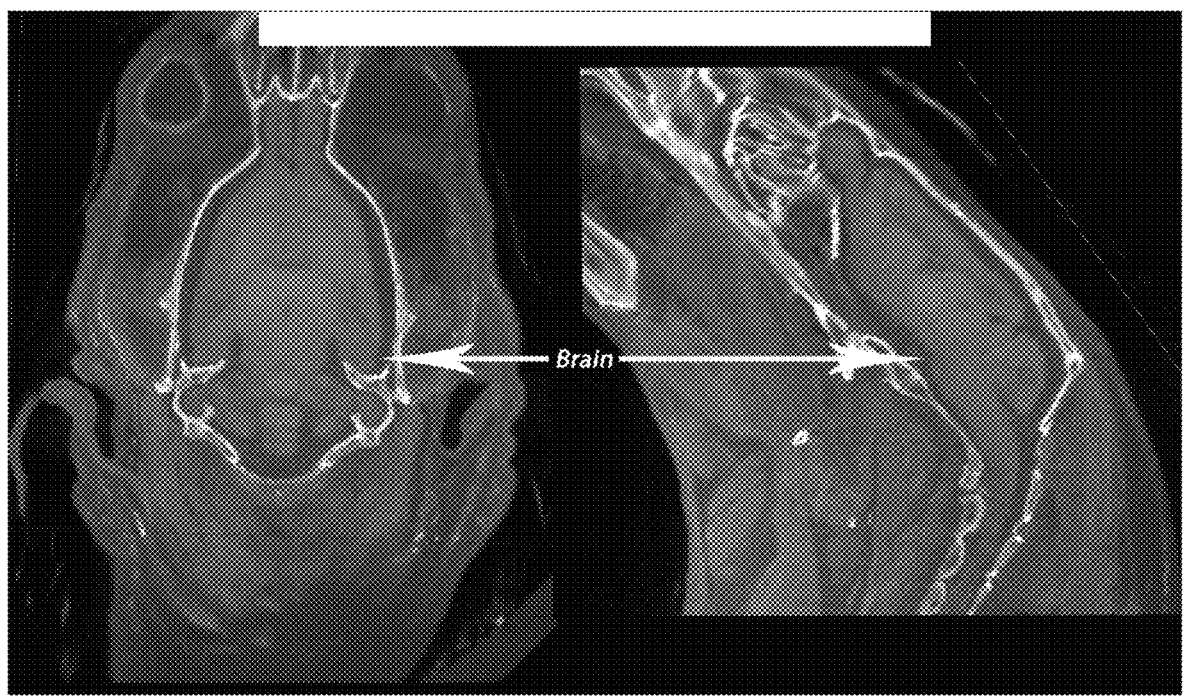
Figure 2J:
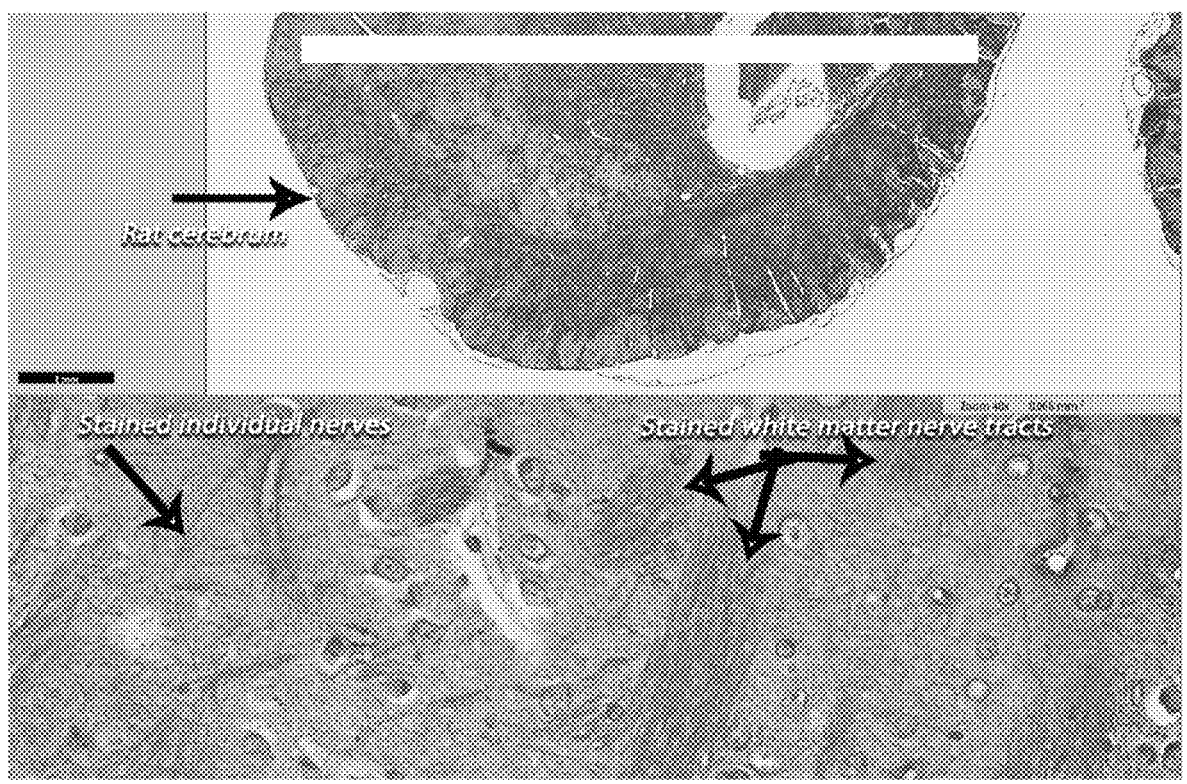
FIG. 2J illustrates histology slides stained with hematoxylin and eosin in accordance with an embodiment of the present invention.

FIG. 2G shows a heparinized rat perfused with an iodine-based contrast agent with carrier agents DMSO and ethanol and then CT-scanned at 200 µm immediately (left in FIG. 2G, transverse plane) and four hours post-contrast (right in FIG. 2G, coronal plane). In the left image, the gyri and sulci of the brain are visible. In the right image, the various structures of the ventral brain are visible. FIG. 2H shows a heparinized rat first flushed with distilled water and then perfused with a silver-based contrast agent (silver nitrate) plus a single carrier agent (DMSO) and then CT-scanned at 200 µm. The left side shows the coronal view of the brain while the right shows the sagittal image. In both images, the brain is readily visible. FIG. 2I features the same rat shown in FIG. 2H, but scanned at 90 µm versus 200 µm. This example shows how finer-resolution imaging improves the details seen. This also demonstrates how the technique of using a contrast agent plus carrier agent evenly distributes the stain across a tissue that is notoriously difficult to stain in situ (the brain). This technique allows for the study of brain, spinal cord, and nervous tissue without physically removing and damaging the tissue. This is especially true when considering damage caused by processing tissues for histology—the most frequently accepted "gold standard" for assessing tissue. FIG. 2J features the same rat shown in FIGS. 2H and 2I using hematoxylin and eosin-stained histology slides (low magnification at top, high magnification at bottom). The histology shows that white matter nerve tracts (seen as bundles of stained fibers) and individual nerves pick up stain and are readily visible. This also demonstrates the differential contrast staining that makes visualization of different brain regions possible with CT scans (see FIG. 2I).

Example 3

Figure 3A:
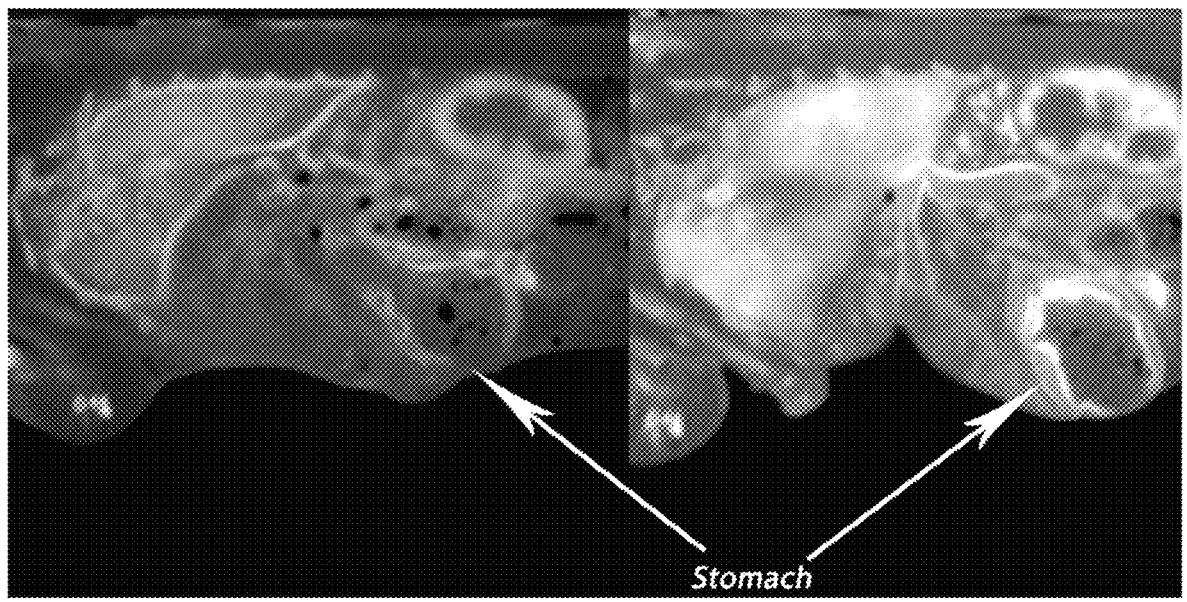
FIG. 3A and FIG. 3B illustrate using an imaging agent to differentiate components of the gastrointestinal system in accordance with embodiments of the present invention.
Figure 3B:
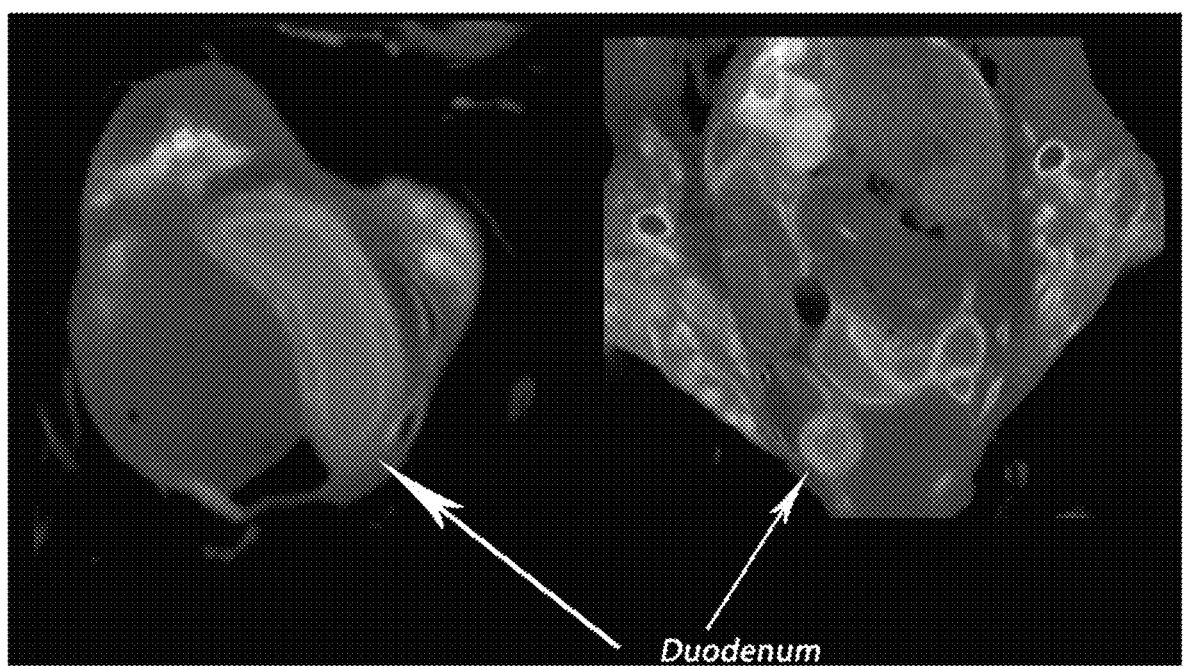

An embodiment of the inventive imaging agent is used to differentiate components of the gastrointestinal system. FIGS. 3A and 3B illustrate the differentiation of different layers of the gastrointestinal system of a subject. In FIG. 3A, a heparinized rat was first flushed with a vascular conditioning agent (METAFLOW and RECTIFIANT) and then perfused with an iodine-based contrast agent, carrier agents DMSO and urea, and an odor-reducing agent (vanilla extract) and then CT-scanned immediately (right in FIG. 3A, sagittal plane) and four hours post-perfusion (left in FIG. 3A, sagittal plane) at 200 µm resolution. The rugal folds of the stomach are readily visible and more radiodense than the submucosa and serosal layers. The kidney is also readily visible in the upper right-hand portion of each image. In both images shown in FIG. 3A, the head is to the left. In FIG. 3B, a Moluccan cockatoo (Cacatua moluccensis) was heparinized, euthanized (with pentobarbital) and then perfused with formalin. Approximately one week later, the body was flushed with an iodine-based stain plus a carrier agent (DMSO). The bird was CT-scanned at 200 µm resolution two hours later. The image on the left of FIG. 3B shows a longitudinal image of the ascending and descending duodenum with the pancreas sandwiched in between. The image on the right of FIG. 3B shows a cross-section of the duodenum. In both examples, the different layers (at least 3 at this resolution) of the intestinal wall are easily recognizable and likely represent the submucosa (inner layer), mucosa (middle layer), and serosa (outer layer).

Example 4

Figure 4A:
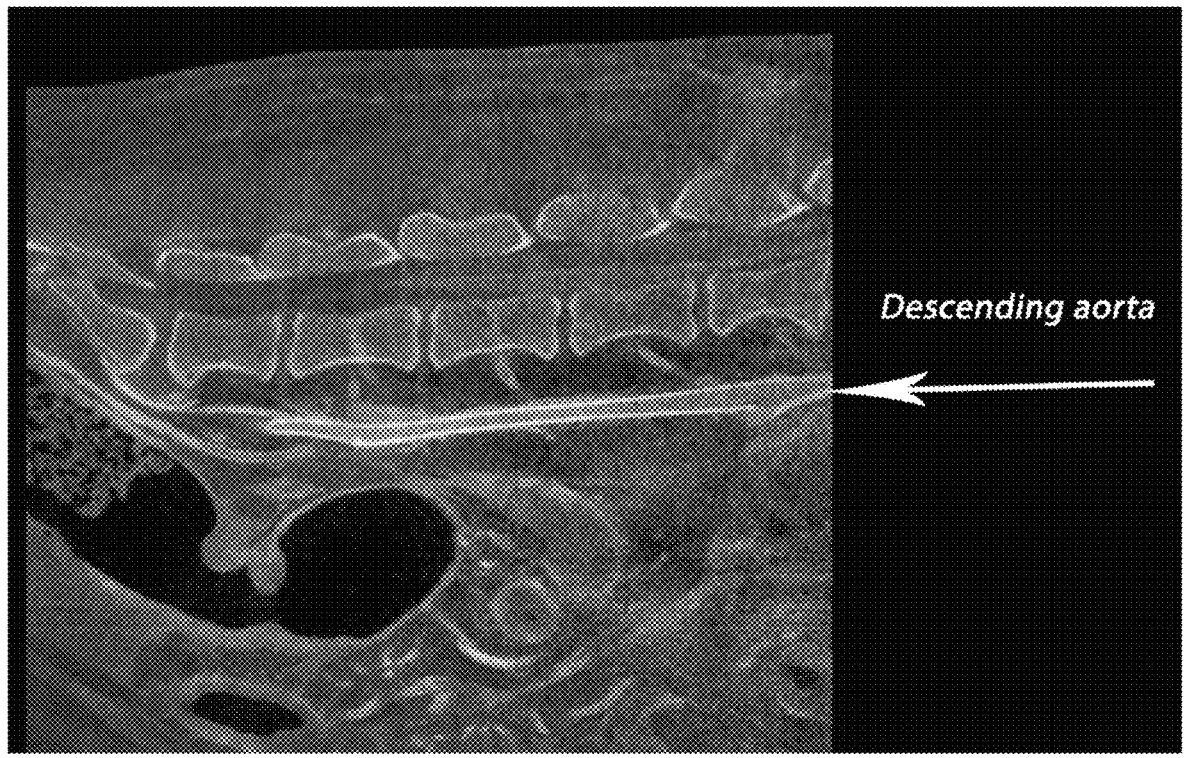
FIGS. 4A-4D illustrate using an imaging agent to differentiate between arteries and veins in accordance with embodiments of the present invention.
Figure 4B:
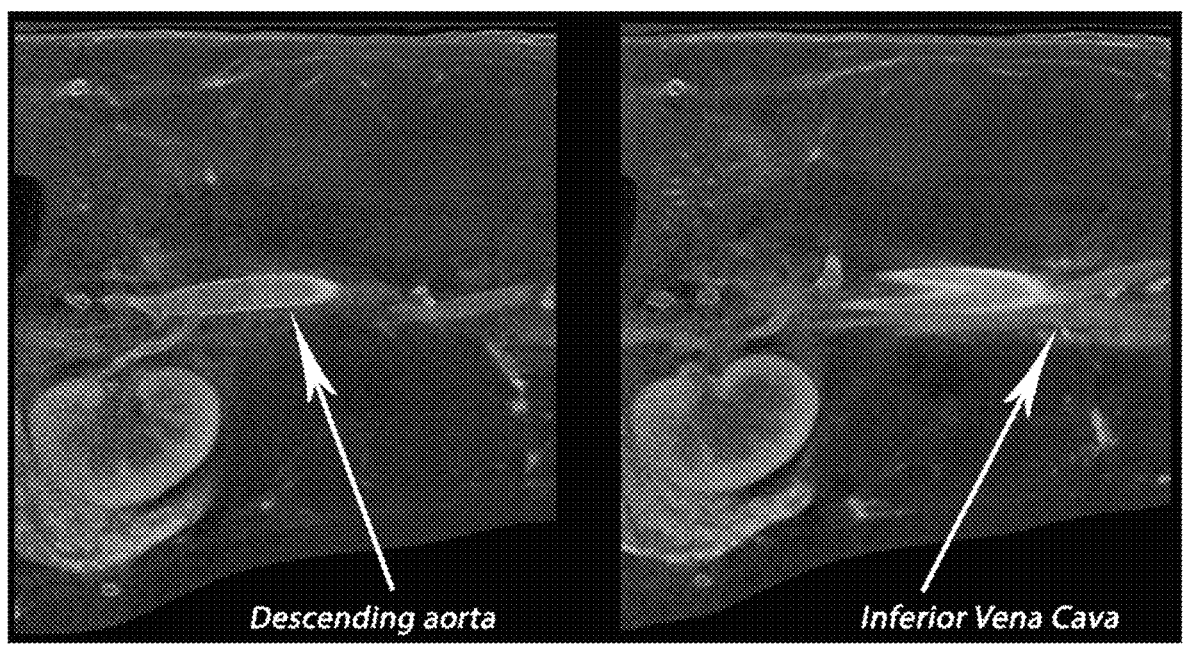

An embodiment of the inventive imaging agent is used to differentiate between arteries and veins and clearly identify the vessel wall and its lumen. Additionally, the imaging agent and process may be used to evaluate complex cardiac anatomy and disease. FIGS. 4A-4D illustrate differentiating between arteries and veins and evaluating the heart using a novel imaging agent system. In FIG. 4A, the golden retriever from FIGS. 2E and 2F is perfused with an iodine-based contrast stain, a secondary contrast stain, carrier agents urea, DMSO, and isopropyl alcohol, and two odor-reducing agents (vanilla extract, orange extract) and CT-scanned two hours later at 200 µm resolution (sagittal section). The descending aorta is readily visible, and the vessel wall (more radiodense or bright) is easily distinguishable from the vessel lumen (less radiodense or darker). The head of the dog is to the right in FIG. 4A. FIG. 4B shows the same dog as in FIG. 4A, but the image is taken immediately post-staining. The descending aorta and the renal artery and their more radiodense walls (and more radiolucent lumens) are readily identified in the left image of FIG. 4B. The right image of FIG. 4B shows the descending aorta and the more ventrally located inferior vena cava. The wall of the inferior vena cava is less dense and thick compared to the approximately same-sized descending aorta. The lumen of the inferior vena cava is still distinguishable from its wall (more radiodense). These images demonstrate how similarly sized arteries and veins can be differentiated by the imaging agent. In general, the arteries have a thicker and more radiodense wall (greater contrast stain uptake) compared to size-matched veins. The kidney is visible in the lower left of each image. The head is to the left in FIG. 4B.

Figure 4C:
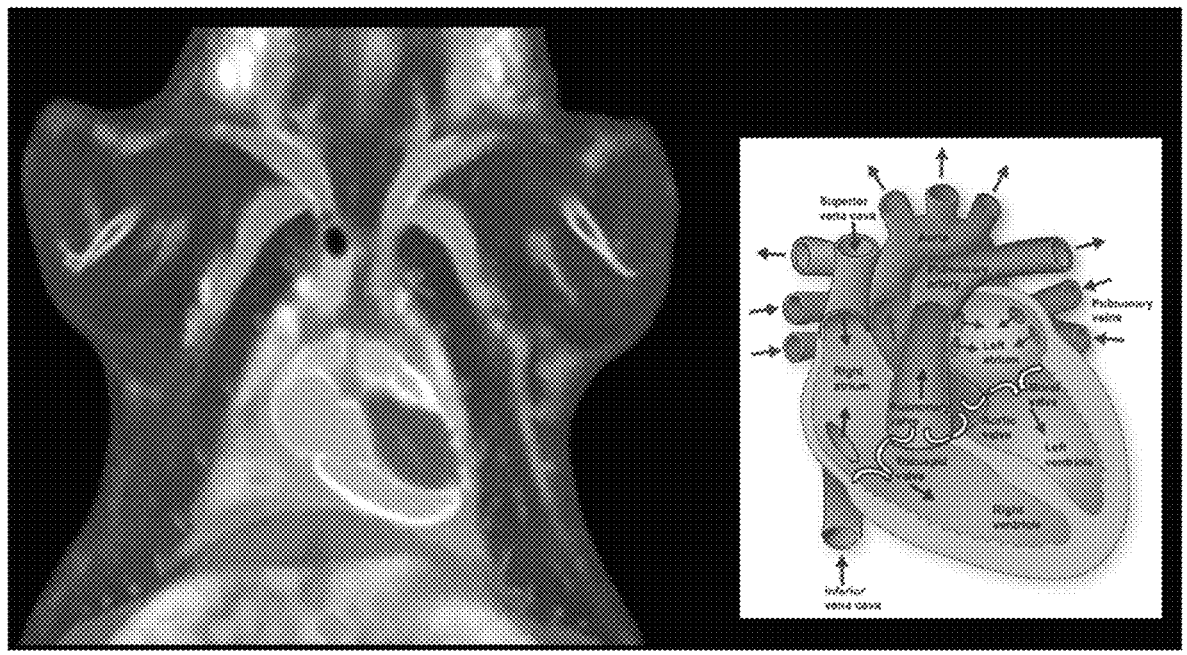
Figure 4D:
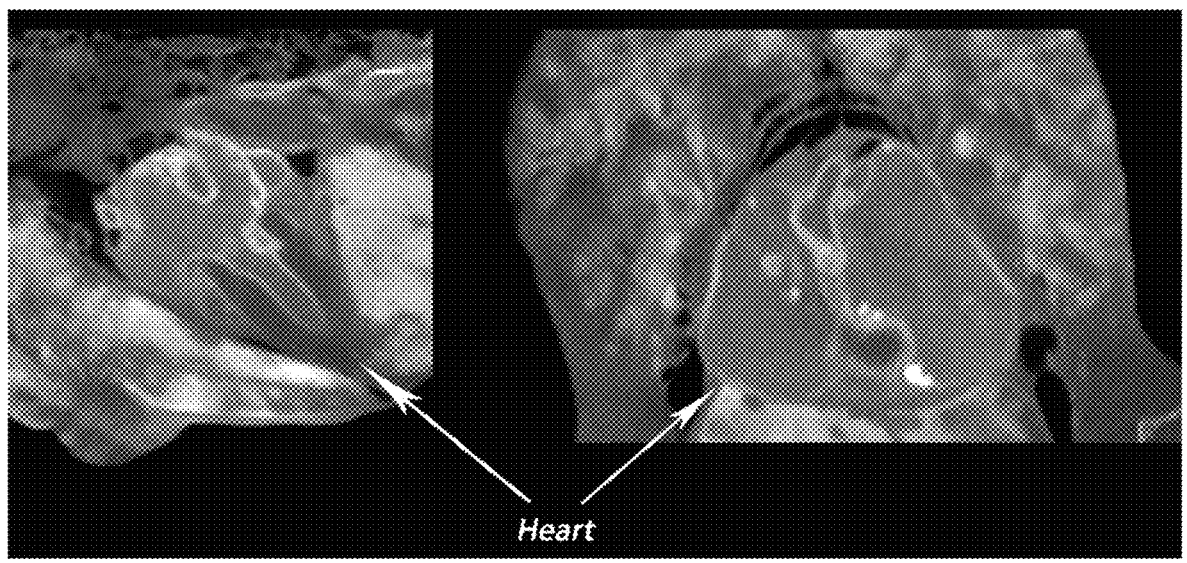

In FIG. 4C, a rat is perfused with an iodine-based contrast stain and carrier agent DMSO and is CT-scanned immediately after perfusion at 200 µm resolution (coronal section). The heart and its four chambers are readily visible (left image of rat). An inset drawing of the heart (right image in FIG. 4C) is used to help viewers identify the chambers of the rat heart. The contrast stain makes complex heart anatomy readily visible and can be used to study normal and abnormal anatomy. In FIG. 4D, the Moluccan cockatoo from FIG. 3B was heparinized, euthanized (with pentobarbital), and then perfused with formalin. Approximately one week later, the body was flushed with an iodine-based stain plus a carrier agent (DMSO). The bird was CT-scanned at 200 µm resolution two hours (left, sagittal section) and five hours (right, coronal section) later. These images show a severely enlarged heart with dilated chambers characteristic of dilated cardiomyopathy. Additionally, the contrast stain has differentially stained the thin heart muscle (bright white) differently than the chamber lumens (light grey) and thicker ventricular muscle (dark grey). These studies provide insight into the type of muscle and other tissue present in failing hearts as each tissue type takes up the contrast stain at different rates.

Example 5

Figure 5A:
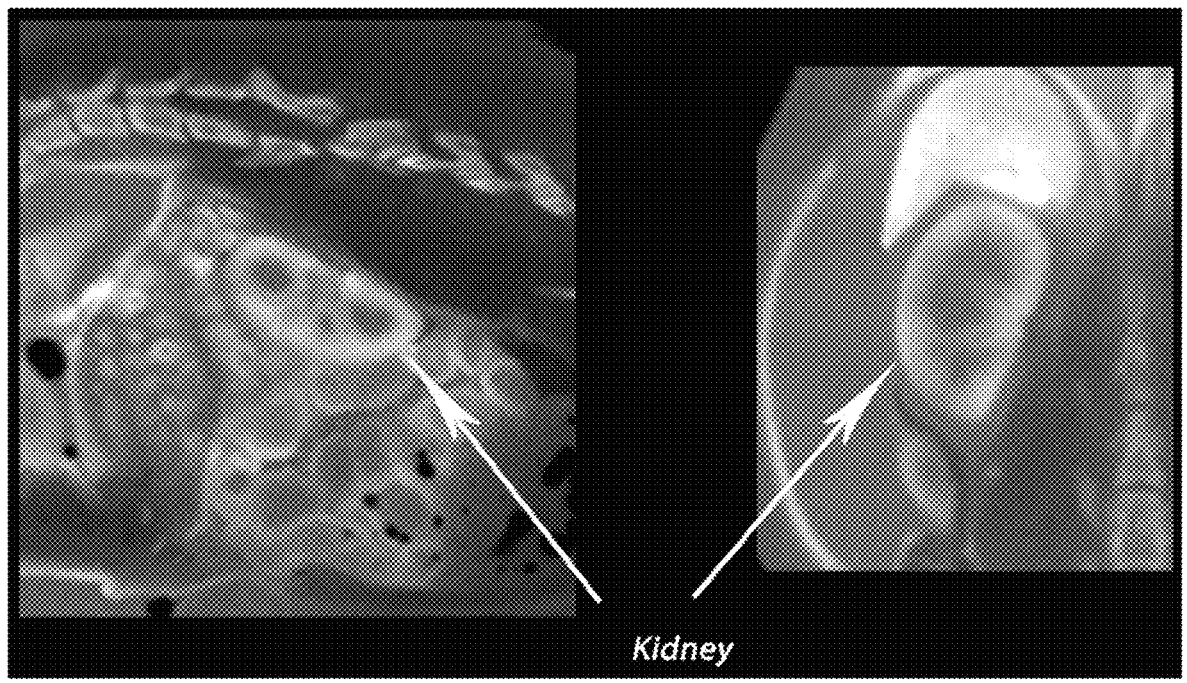
FIGS. 5A and 5B illustrate using an imaging agent to identify renal anatomy in accordance with embodiments of the present invention.
Figure 5B:
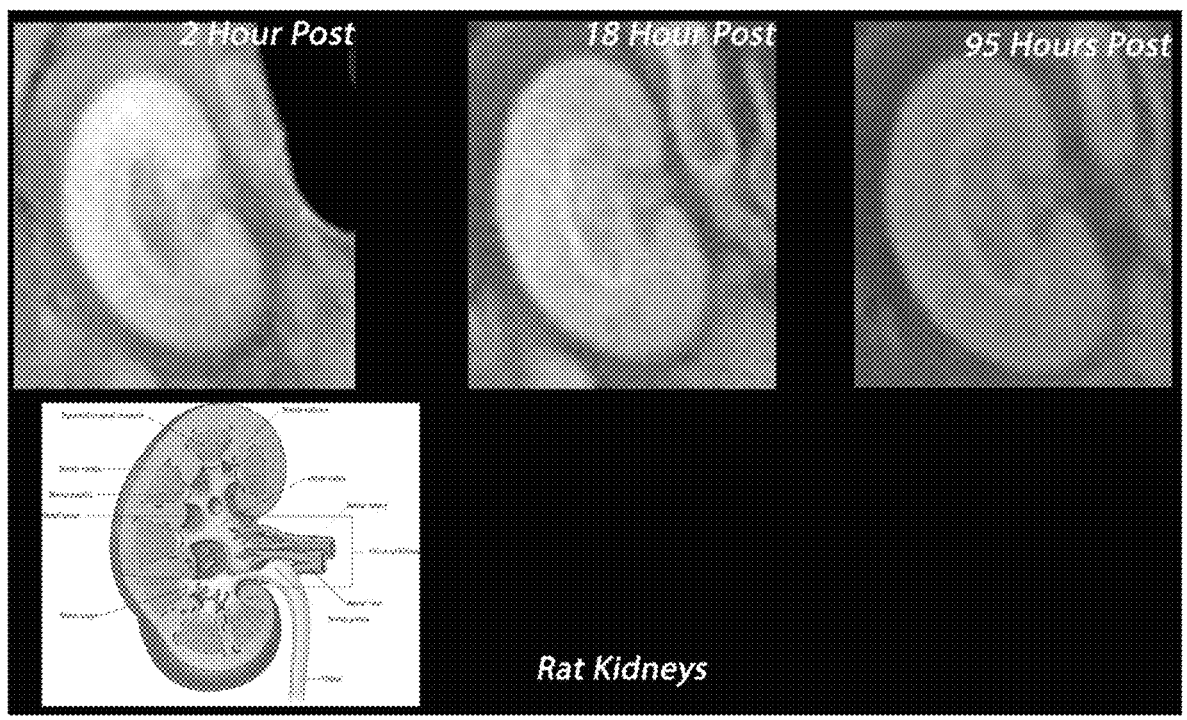

An embodiment of the inventive imaging agent is used to define kidney anatomy. FIGS. 5A and 5B illustrate using the imaging agent to identify renal anatomy in accordance with embodiments of the present invention. In FIG. 5A, a rat is flushed with a vascular conditioning agent (METAFLOW and RECTIFIANT) and then perfused with an iodine-based contrast agent, carrier agents urea and DMSO, and two odor-reducing agents (vanilla extract and orange extract). The rat is CT-scanned at 200 µm resolution four hours later (left in FIG. 5A, sagittal plane) and rat perfused with an iodine-based contrast agent and carrier agent and then scanned two hours later at 200 µm resolution (right in FIG. 5B, coronal plane). The renal pelvises and pyramids are more clearly defined in the rat on the left compared to the right. Renal anatomy is still well defined in the example on the right. This comparison shows how adjustment in the protocol can be used to improve definition of various target tissues. In FIG. 5B, a rat is perfused with silver-based contrast agent with carrier agents urea and DMSO and two odor-reducing agents (vanilla extract and orange extract). The rat was CT-scanned at 200 µm resolution in the same plane at 2, 18, and 95 hours post-contrast perfusion and euthanasia. A bottom left inset image of the rat kidney is used as a reference. The differentiation of the portions of the kidney becomes more pronounced over time. For example, there is a distinct radiodense (white) line separating the renal medullary region from the pelvis region that is more evident in the "95 Hours Post" image compared to that of the "2 Hours Post" image.

Example 6

Figure 6A:
FIGS. 6A-6D illustrate using an imaging agent to identify plant structures in accordance with embodiments of the present invention.
Figure 6B:
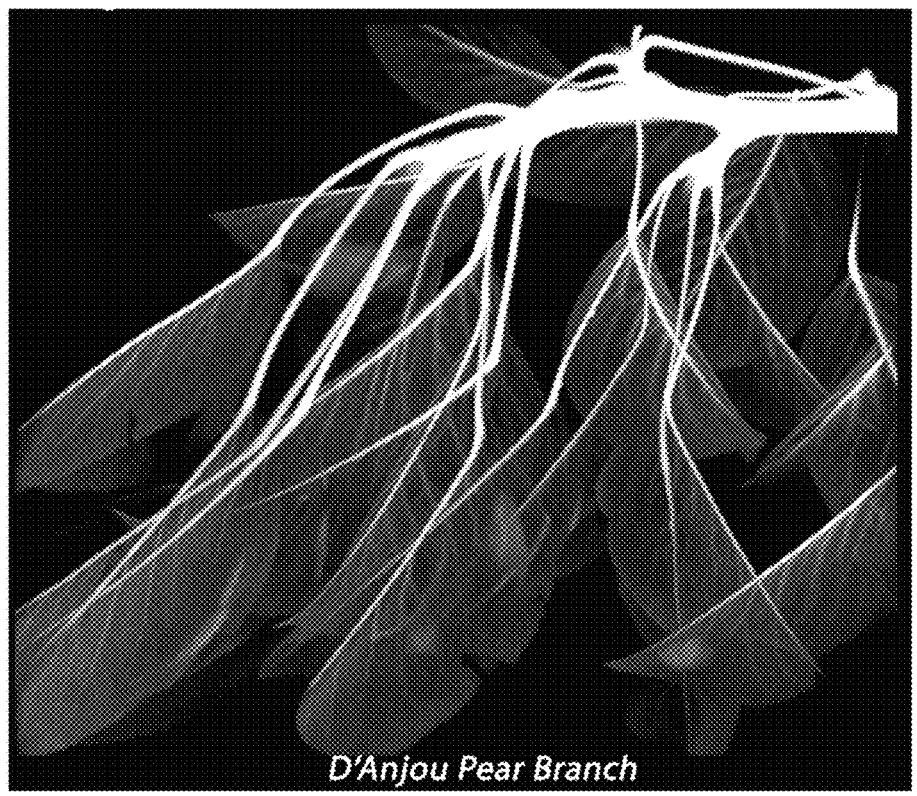
Figure 6C:
Figure 6D:
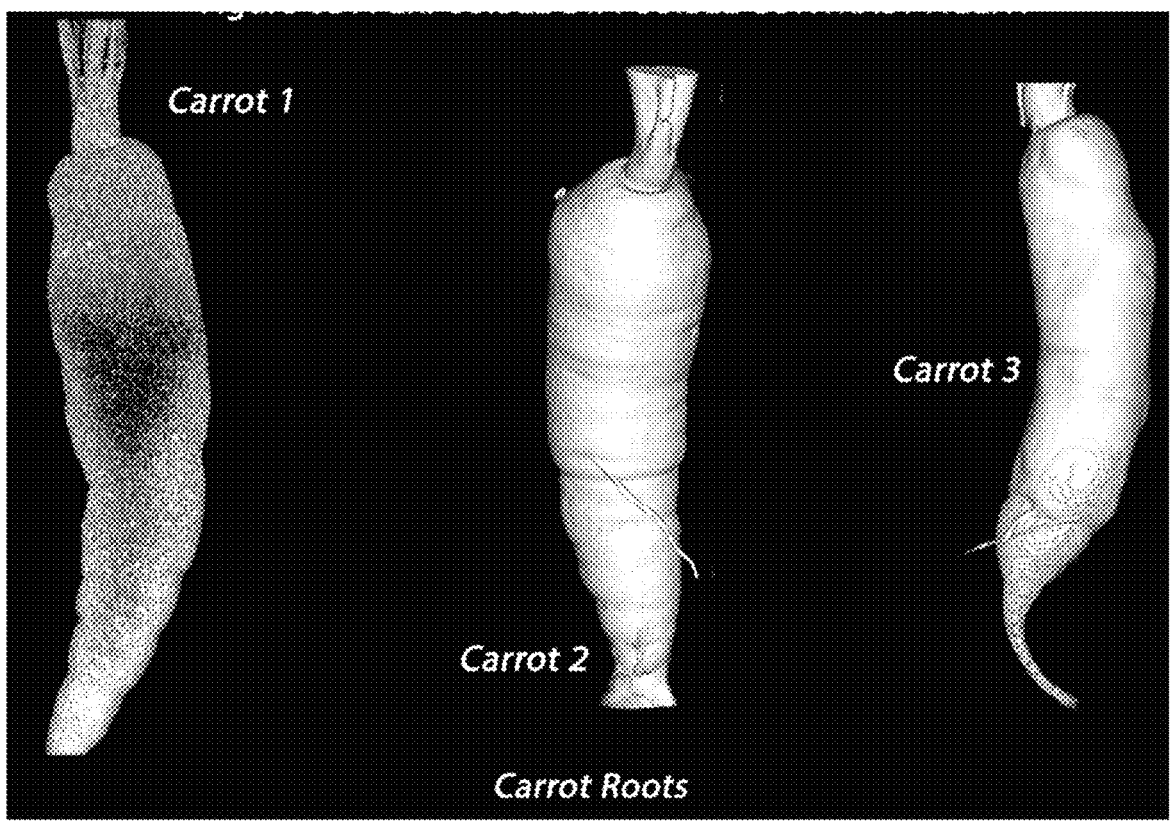

An embodiment of the inventive imaging agent is used to define plant structures. FIGS. 6A-6D illustrate using the imaging agent to identify plant structures. FIG. 6A shows a radiograph of a flowering snapdragon (left image in FIG. 6A, left side) and marigold (left image in FIG. 6A, right side, and right image in FIG. 6A with blown up view of the flower) were suspended in a beaker filled with an iodine-based contrast stain, carrier agents DMSO, ethanol, and urea, and two odor-reducing agents (vanilla extract and orange extract) with roots below the fluid line. The stems, leaves and flowers of both plants were not allowed to come into direct contact with the contrast solution. The plants readily took up the radiodense solution clearly providing contrast and outlining all portions of the plant including the stem, leaves and flowers. FIG. 6B shows a cut D'Anjou pear branch soaked in a solution of iodine-based contrast agent and carrier agents DMSO and ethanol and then CT-scanned 23 hours later. The contrast agent can easily be seen outlining the stems to the leaves. FIG. 6C shows a cut Tomatillo branch soaked in a solution of potassium iodide-based contrast agent, carrier agents DMSO and ethanol and then CT-scanned 28 hours later. FIG. 6D shows a comparison of a plant with soaking in 5% iodine (75%) and water (25%)— the addition of the carrier solution (carrier agents DMSO and ethanol and two odor-reducing agents (orange and vanilla extracts)) significantly improves the diffusion of the stain across the plant subject. "Carrot 1" was soaked in an iodine/water-only solution, "carrot 2" was soaked in one form of iodine plus carrier solution, and "carrot 3" was soaked in a different form of iodine plus carrier solution all for approximately 24-28 hours and then CT-scanned at 150 µm resolution. "Carrot 2" and "carrot 3" are diffusely stained while "carrot 1" is unevenly stained. These images demonstrate why the contrast agent alone is not enough to evenly and diffusely stain the plant subject. The addition of the carrier agent improves the distribution of the contrast stain within the plant.

Example 7

Figure 7A:
FIGS. 7A-7C illustrate using a metallic (e.g., silver-based) imaging agent to highlight specific structures in accordance with embodiments of the invention.

An embodiment of the inventive imaging agent uses metallic (e.g., silver-based) compounds that are combined with an aforementioned carrier agent and a solubilizing or permeabilizing agent and perfused into the subject to highlight specific structures. In one embodiment, silver-based compounds (2.5-50%) are combined with an aforementioned carrier agent (silver-based compound 2.5-90% to carrier agent v/v) and perfused into the subject. For example, the combined product can be perfused into the cardiovascular system. The carrier agent then carries the silver-based compound through the vascular system and into the target tissues. Due to the density of the metallic compound, the targeted tissue is then "visible" using X-ray technology such as with CT scanning. FIG. 7A shows a rat perfused with a silver-based contrast agent plus carrier agent (DMSO) plus two odor-reducing agents (urea and vanilla extract). (Here, in lower concentrations, urea acts as an odor-reducing agent rather than as a carrier agent.) Eight hours post-perfusion and euthanasia, the heart and its chambers are readily visible (left). Also, the descending aorta with its radiodense (white) arterial wall is differentiated from its radiolucent (black)

lumen. These images demonstrate how this imaging agent differentially stains separate components of the heart and vasculature.

Figure 7B:
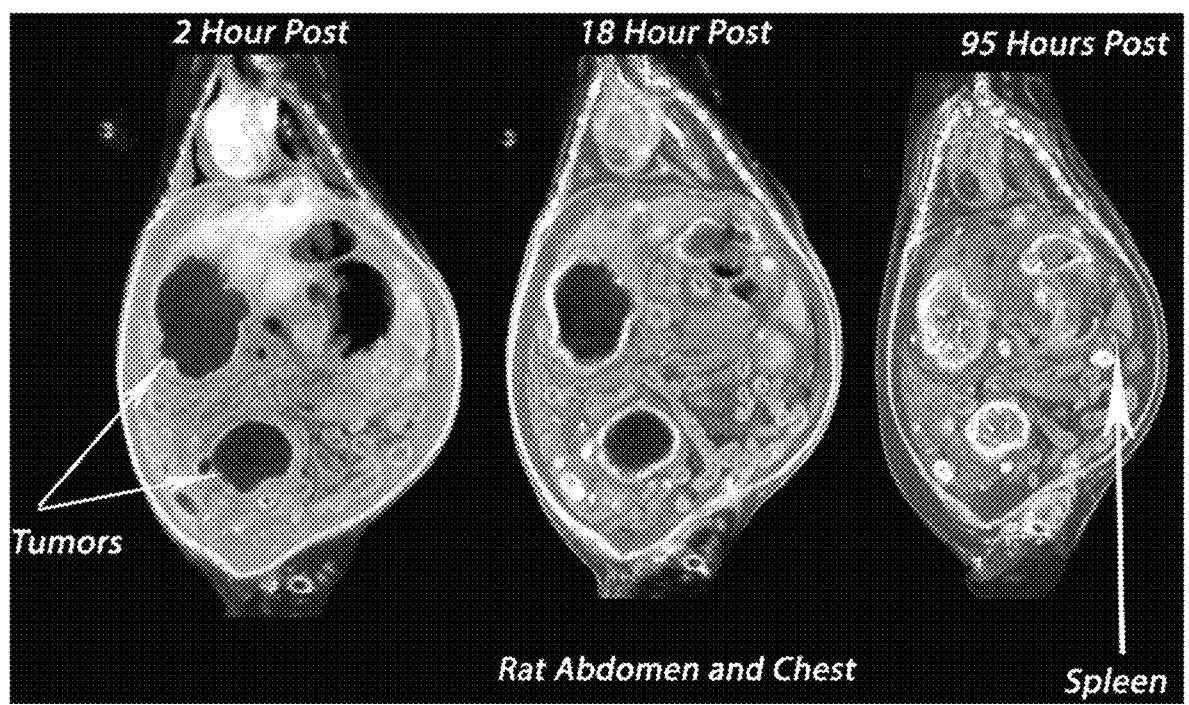
Figure 7C:
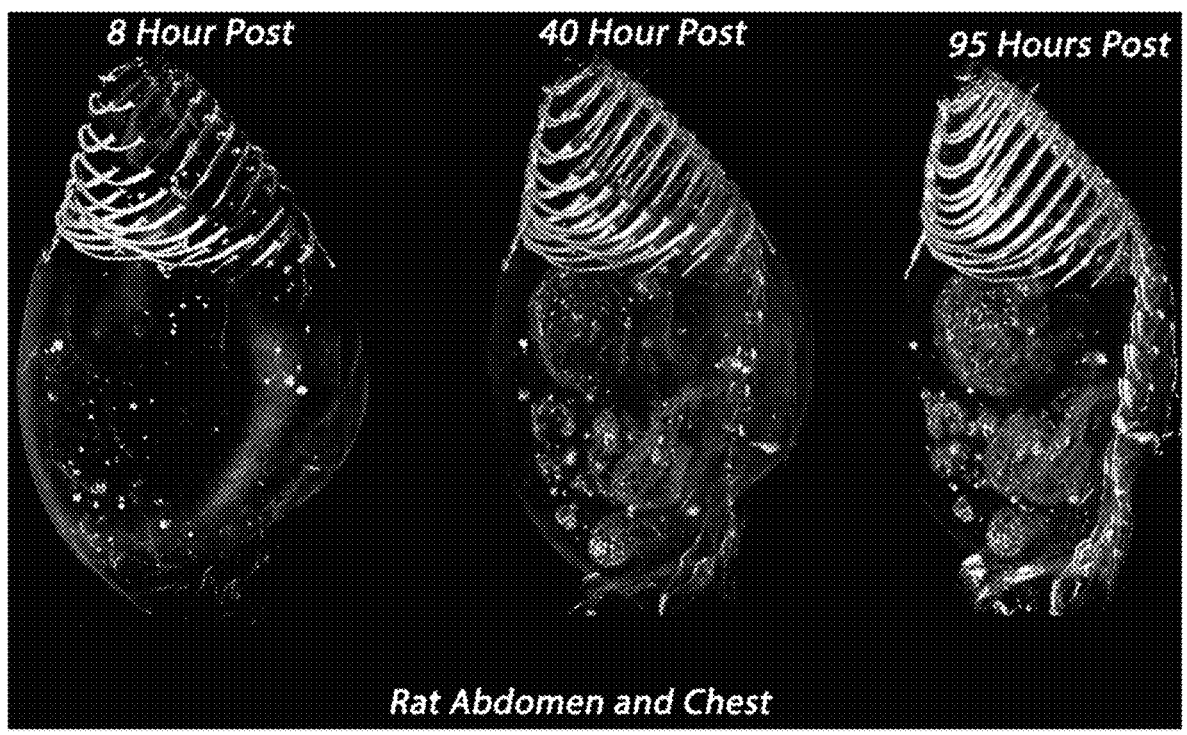

The same approach may be used to visualize cancer. In FIG. 7B, a planar view, a rat is perfused with a silver-based contrast agent, carrier agent DMSO, and two odor-reducing agents (urea and vanilla extract). The rat was CT-scanned at 200 µm resolution in the same plane at 2, 18, and 95 hours post-contrast perfusion and euthanasia. This rat had metastatic carcinomatosis that is evident as large radiolucent (black) space occupying masses within the abdomen at "2 Hours Post" staining. As time goes on, the cancers become more visible first by the radiodense (white) capsule at "18 Hours Post" staining. By "95 Hours Post" staining, both the capsule and the interior of the tumors are taking up the contrast stain making the entire structure of the tumor visible. Even the triangular spleen takes up more radiodense stain over time. In FIG. 7C, a volumetric view, the same rat as in FIG. 7B is visualized with color enhancement. CT scans were taken at 8, 40, and 95 hours post-contrast perfusion and euthanasia. As time progresses, the cancer cells take up more contrast stain making their numeric and volumetric quantification readily visible. This process allows for virtual autopsy/necropsy and with computer recognition software can dramatically speed the rate of tumor detection over traditional thin slicing, histopathology, and individual slide review.

Example 8

Figure 8:
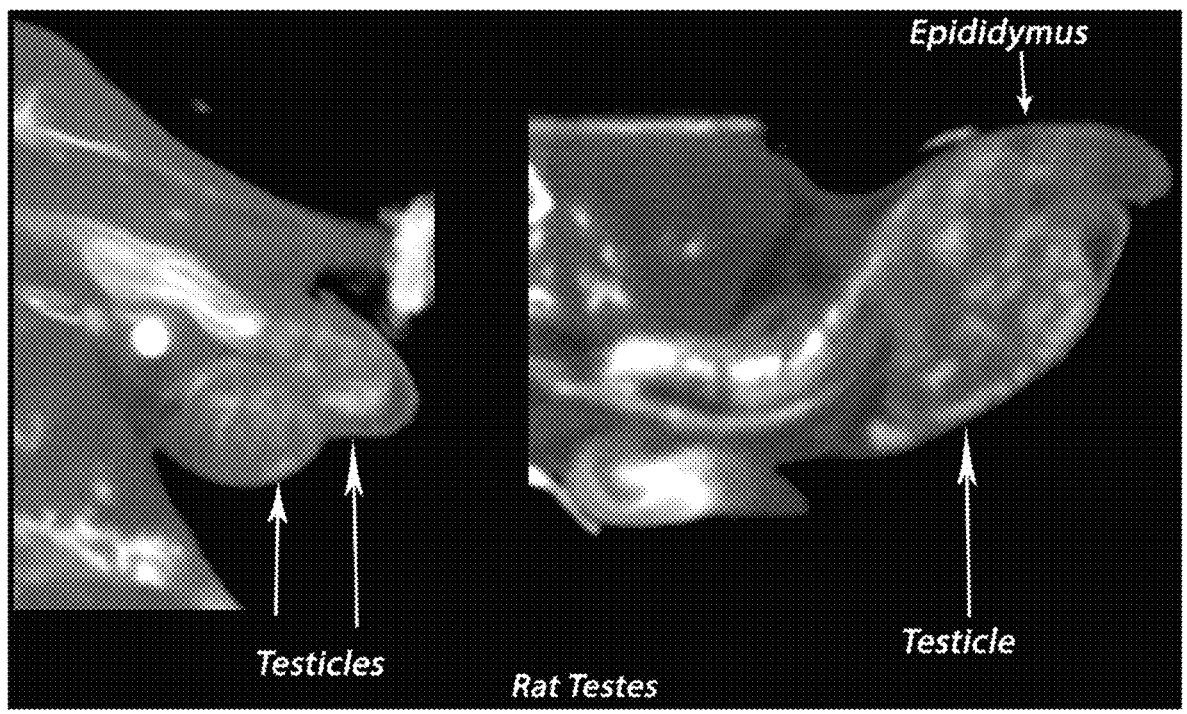
FIG. 8 illustrates using an imaging agent to non-destructively stain reproductive organs in accordance with embodiments of the present invention.

The inventive imaging agent may be used to non-destructively stain reproductive organs. FIG. 8 shows a rat that was perfused with an iodine-based contrast agent plus carrier agents urea, ethanol, and DMSO plus two odor-reducing agents (vanilla and orange extracts) after the vasculature was flushed with vascular conditioning agents (PROFLOW and RECTIFIANT). The testicles are readily stained immediately after IV perfusion with the imaging agent. The left image of FIG. 8 shows the cross-section of both testes while the right image of FIG. 8 shows a longitudinal image of a single testicle with the main testicular tissue on the bottom and epididymis on top.

Example 9

Figure 9A:
FIGS. 9A-9C illustrate using an imaging agent to stain muscles in accordance with embodiments of the present invention.
Figure 9B:
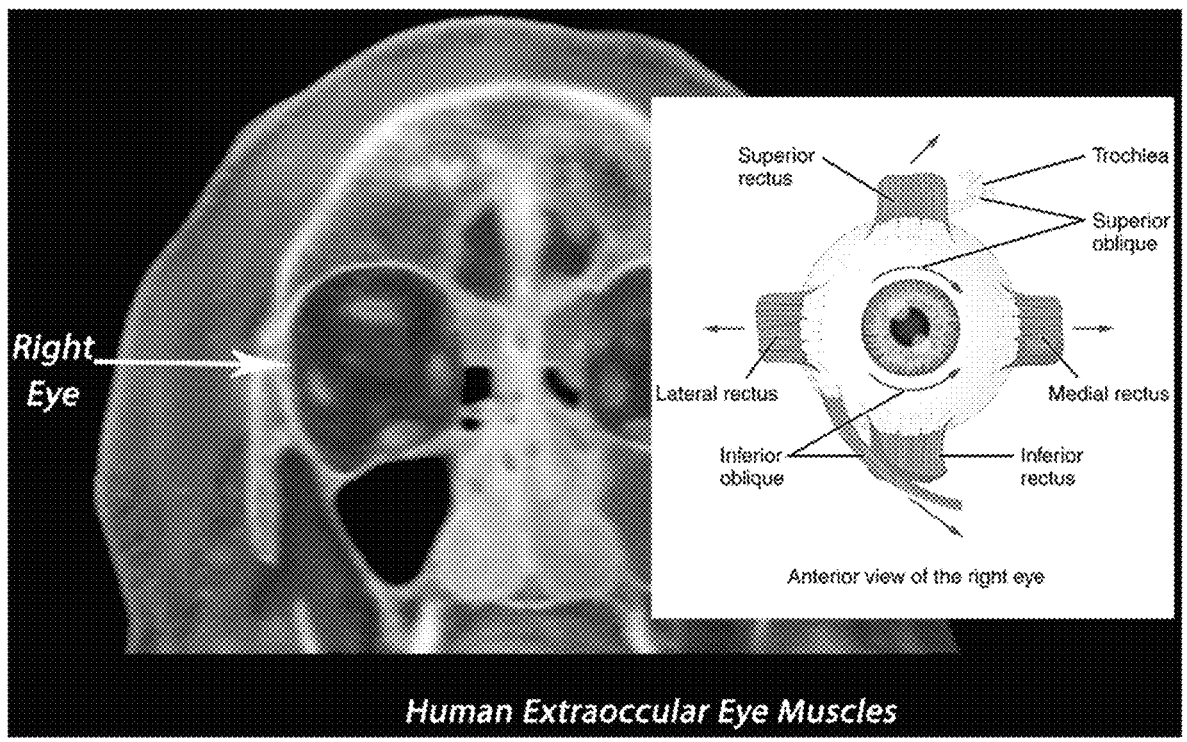
Figure 9C:
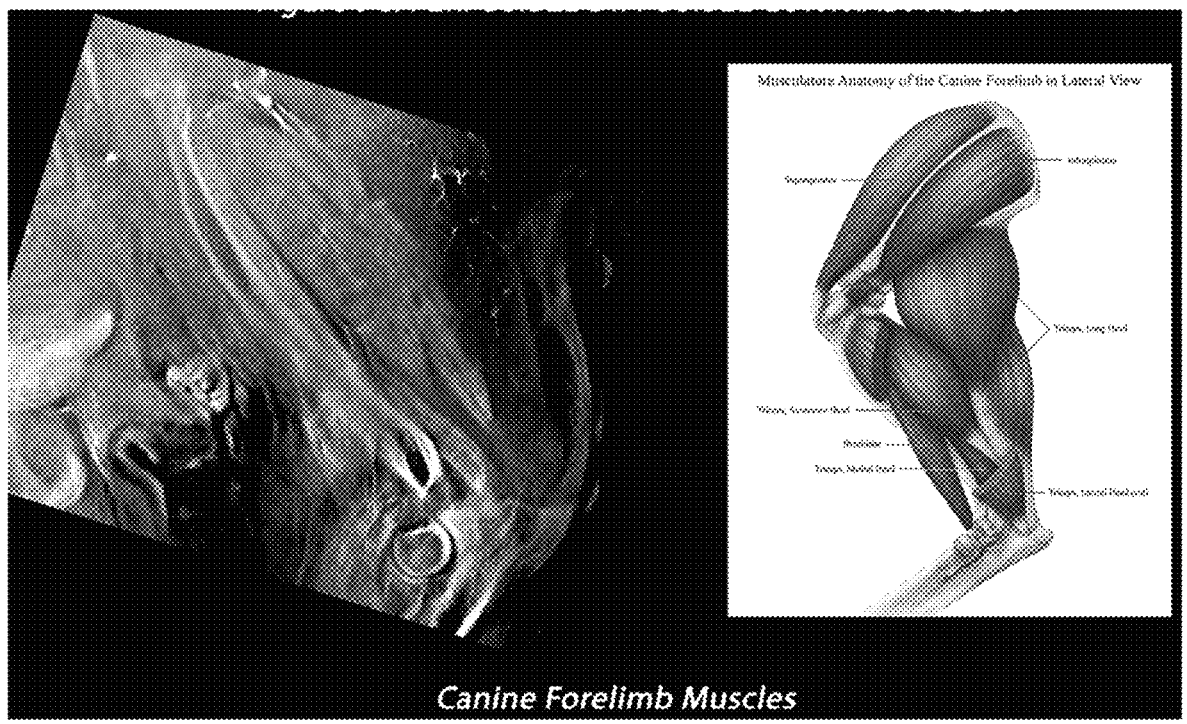

An embodiment of the inventive imaging agent is used to stain muscles. In FIG. 9A, the human cadaver from FIG. 2C is shown flushed with saline solution and then perfused with an iodine-based contrast agent, carrier agents DMSO, urea, and ethanol, and two odor-reducing agents (vanilla and orange extracts). The gluteus maximus muscle (compare to inset image) is readily visible. In FIG. 9B, the head of the human cadaver is shown from the whole body perfusion of FIG. 9A. The four main extraocular muscles are readily visible on this coronal plane view of the right eye (compare to the inset image of a right eye). In FIG. 9C, the euthanized golden retriever from FIGS. 2E and 2F is shown. The dog's vascular system was flushed with 0.9% saline followed by an iodine-based contrast stain plus carrier agents urea, DMSO, and isopropyl alcohol, and two odor-reducing agents (vanilla extract, orange extract). The vascular system was then flushed/perfused with a radiopaque, non-diffusible contrast agent (BRITEVU®, Scarlet Imaging). The muscles of the caudal proximal forelimb are readily visible (compare with inset image). These types of images allow for detailed study of muscular origin, insertion, shape, size, disease states, etc., and can be used with normal and abnormal tissue.

Example 10

Figure 10A:
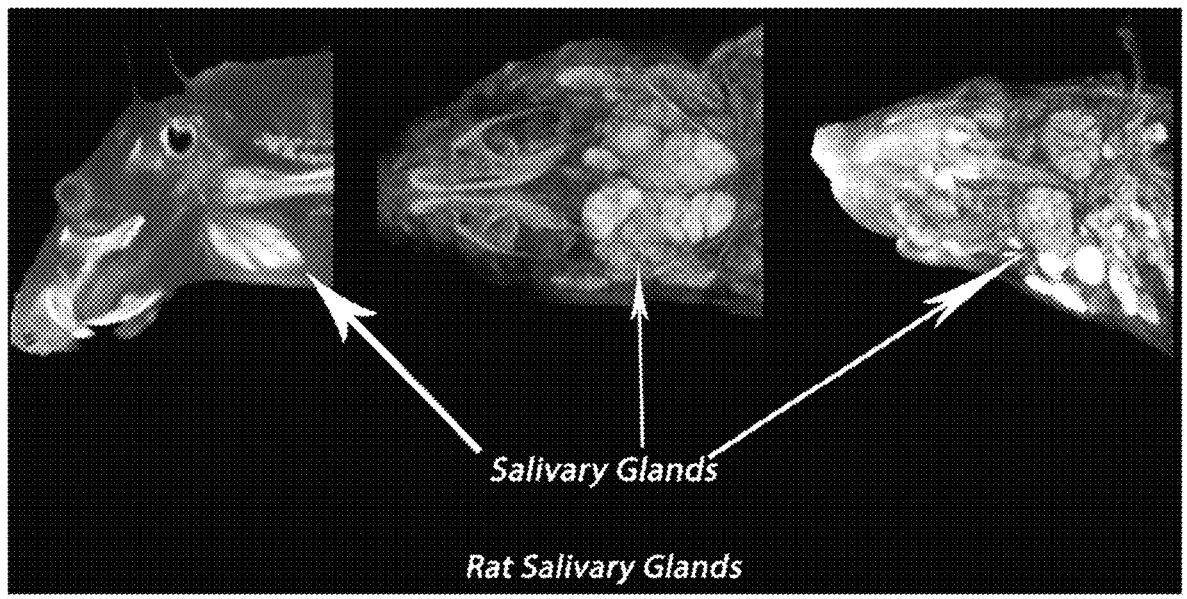
FIGS. 10A-10B illustrate visualization and differentiation of the lymphatic system and glands using an imaging agent in accordance with embodiments of the present invention.

An embodiment of the inventive imaging agent is used for visualization and differentiation of the lymphatic system and glands. The lymphatic system, in particular, is very difficult to perfuse due to the very small size of the lymphatic channels. In the left image in FIG. 10A, a rat is IV (intravenous) flushed with a vascular conditioning agent (PROFLOW and RECTIFIANT) and then perfused with an iodine-based contrast agent, a carrier agent (DMSO), and two odor-reducing agents (urea and vanilla extract) and CT-scanned at 200 µm resolution at two hours post-perfusion (lateral view of head). In the center image in FIG. 10A, a rat is IV flushed with a vascular conditioning agent (PROFLOW and RECTIFIANT), then an alcohol-based preservative and then perfused with an iodine-based contrast agent, a carrier agent (DMSO), and two odor-reducing agents (urea and vanilla extract) and CT-scanned at 200 µm resolution for two hours post-perfusion (maximum intensity projection, ventral view of head). In the right image in FIG. 10A, a rat is IV flushed with saline and then perfused with an iodine-based contrast agent, carrier agents (DMSO and alcohol), and two odor-reducing agents (urea and vanilla extract) and CT-scanned at 200 µm resolution immediately post-perfusion (maximum intensity projection, ventral lateral oblique of head). In all images of FIG. 10A, left is rostral and right is caudal, and the salivary glands are readily visible.

Figure 10B:
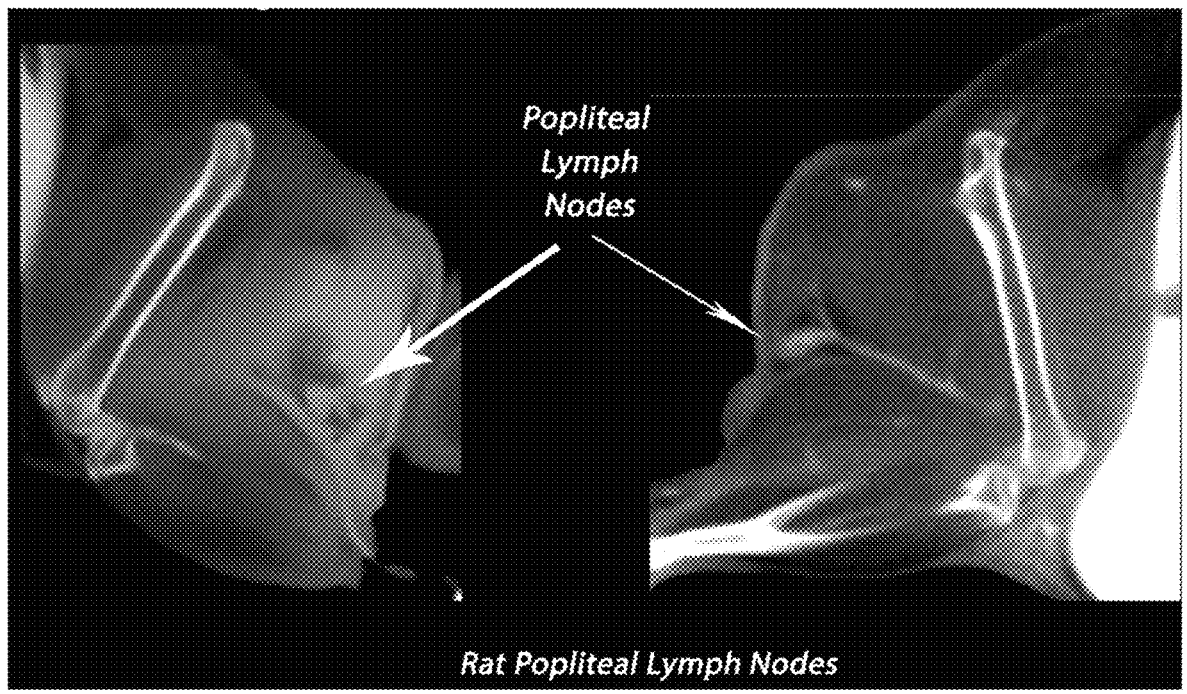

In the left image in FIG. 10B, a rat is IV perfused with a mixture of a potassium iodide-based stain, carrier agents DMSO, urea, and ethanol, two odor-reducing agents (vanilla and orange extracts), and epinephrine and scanned at 200 µm resolution for 18 hours post-perfusion (rear leg lateral view). In the right image in FIG. 10B, a rat is perfused with ISOVUE-370 IV contrast agent, carrier agent DMSO, and two odor-reducing agents (vanilla extract and urea) and CT-scanned at 200 µm resolution for two hours post-perfusion (rear leg lateral view). The rat on the left of FIG. 10B has its head to the left while the rat in the right image of FIG. 10B is facing to the right. The popliteal lymph nodes are highlighted in both images.

Example 11

Figure 11A:
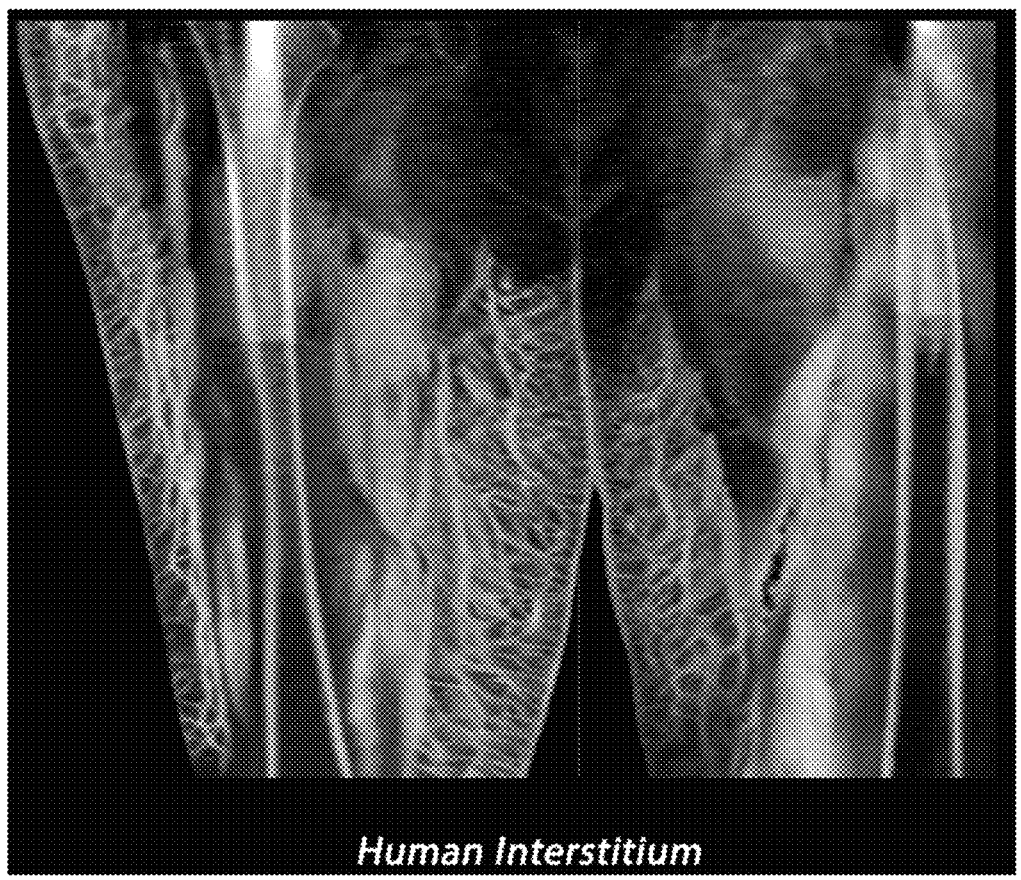
FIGS. 11A-11B illustrate using an imaging agent to study the interstitium in accordance with embodiments of the present invention.
Figure 11B:

An inventive embodiment of an imaging agent is used to study the interstitium. The interstitium is considered a "new organ," but it has been very difficult to study due to its location and collapsible nature. Petros Benias et al., *Structure and Distribution of an Unrecognized Interstitium in Human Tissues*, 8 Scientific Reports, Article number 4947 (2018). "[T]he existence, location, and structure of larger inter- and intra-tissue spaces is described only vaguely in the literature." Id. at 1. The interstitium is notoriously difficult to identify without damaging the tissue. With the contrast stains and methods described in this application, the interstitium can be visualized. FIG. 11A shows the 89-year-old, female human cadaver from FIG. 2C systemically IV perfused with an iodine-based stain, carrier agents DMSO, urea, and ethanol, and two odor-reducing agents (vanilla extract, orange extract) one week after death and then CT-scanned one hour post-perfusion at 0.625 mm (coronal view of the thighs). The interstitium is readily visible as a trabecular network between the skin and the thigh muscles. The femurs can be seen at the center of each leg. FIG. 11B shows the same cadaver as in FIG. 11A with only the thorax and arms visible in coronal view. The trabecular network of the interstitium is readily visible around the arms and shoulders. The heart and lungs are also readily visible in the chest region. While Benias et al. described using confocal laser endomicroscopy of biopsied tissues to identify interstitial tissues, the method and stain described herein allow for visualization of this tissue (organ system in some cases) in situ allowing for non-destructive study of the whole subject. This method further shows the interrelationship between all tissues, which is not possible with a biopsied segment.

Example 12

Figure 12:
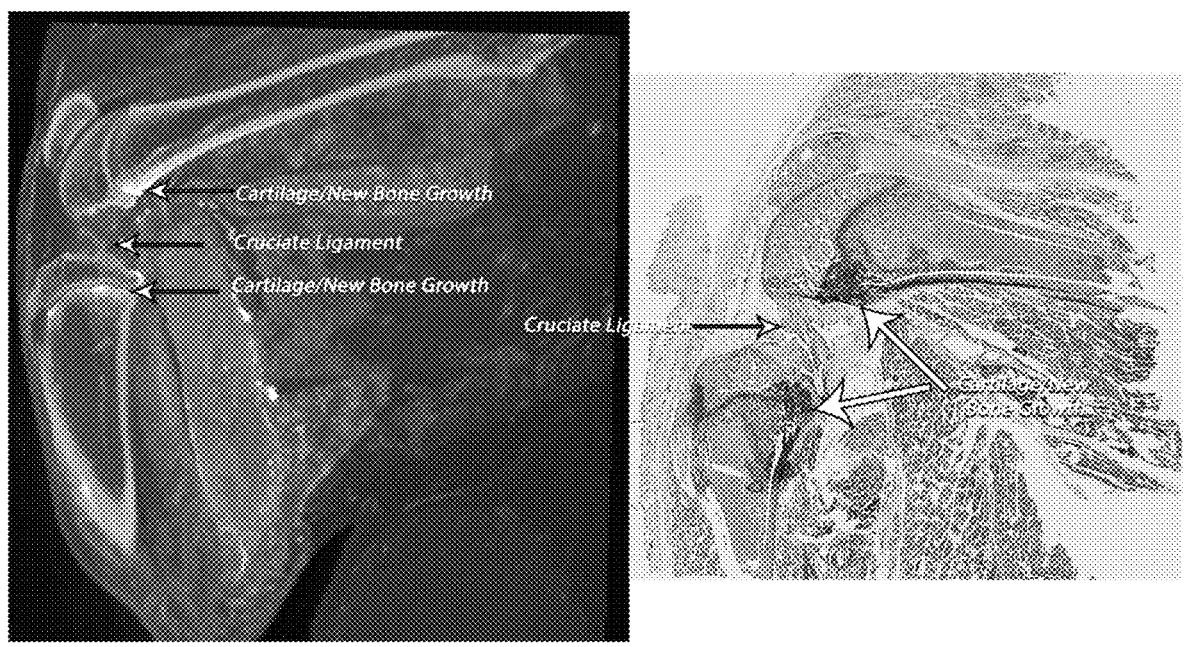
FIG. 12 shows a rat knee using a micro-CT scanner and with hematoxylin and eosin stain histology in accordance with embodiments of the present invention.

FIG. 12 shows a rat knee scanned at 90 μm on a micro-CT scanner (left) and with hematoxylin and eosin stain histology (right). The rat was systemically flushed of blood and then perfused with a silver-based contrast agent plus a carrier agent (DMSO). The process resulted in diffuse and even staining throughout the body. The cruciate ligament stained lightly compared to the intense (bright white left and dark right) staining of the new bone growth and cartilage of the distal femur (top bone in both images) and proximal tibia (bottom bone in both images). This method demonstrates the ability to evenly stain two tissues notoriously difficult to stain in situ—ligament and bone. The surrounding muscles and other tissues are also differentially stained.

Example 13

Figure 13A:
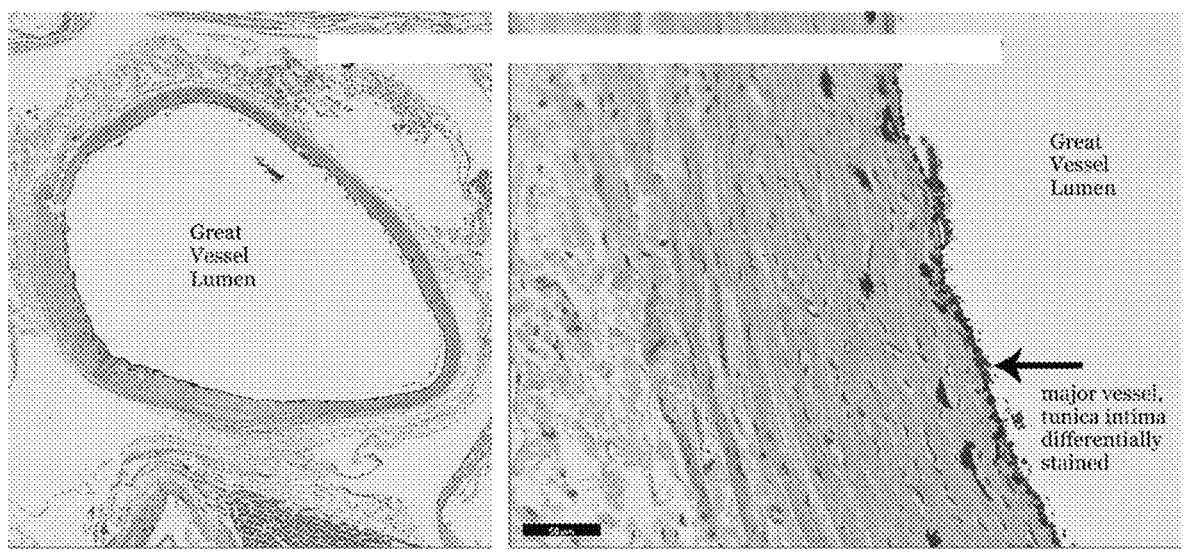
FIGS. 13A-13B illustrate differential staining of a rat great blood vessel in accordance with embodiments of the present invention.
Figure 13B:
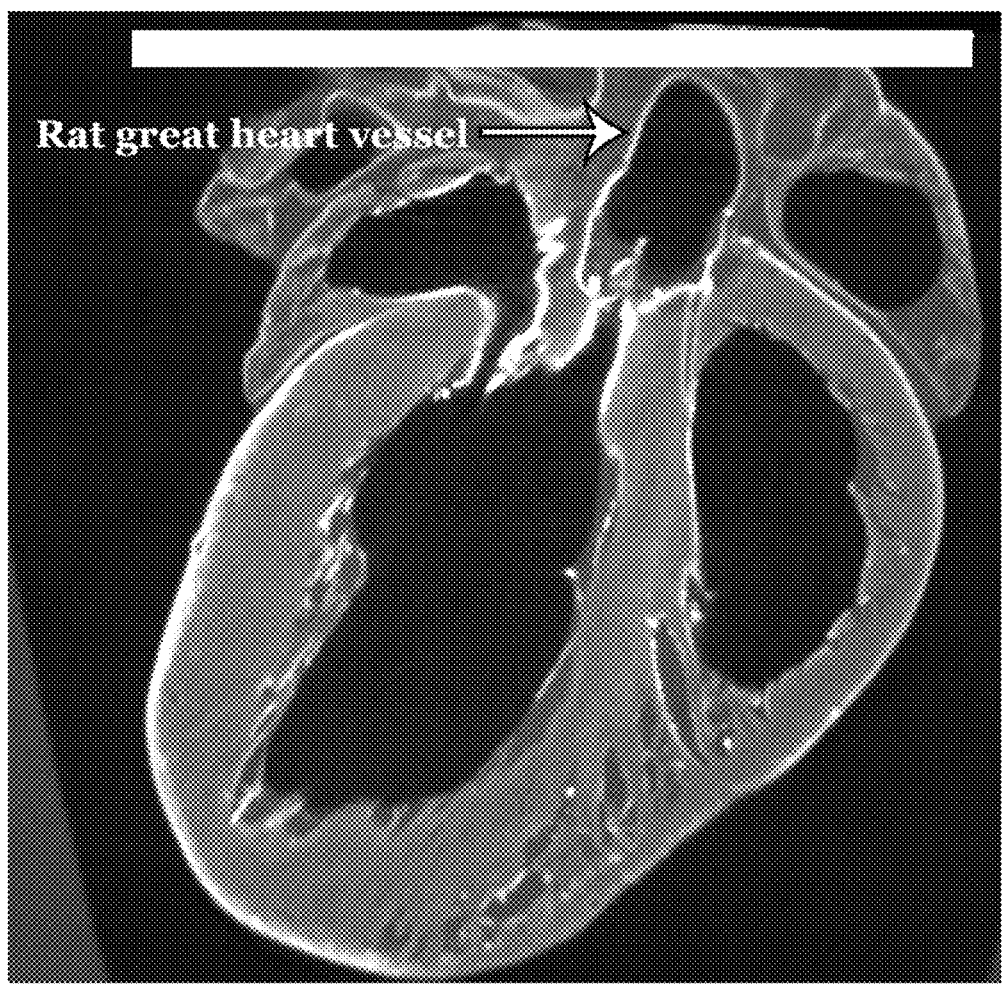

FIG. 13A shows low magnification (left image) and high magnification (right image) images of a rat great blood vessel as viewed in standard hematoxylin and eosin stained histology slides. The rat was first flushed of blood and then perfused with a silver-based contrast agent plus carrier agent (DMSO). The histology shows that vessel tunica intima (innermost layer) takes up a significant portion of the stain while deeper layers (tunica media and tunica adventitia) take up less stain. This produces differential staining and allows one to preferentially see lesions in different layers of the vessel wall (especially along the tunica intima). FIG. 13B shows a 50 μm micro-CT scan of an excised rat heart corresponding to the same histology of FIG. 13A. The heart was stored in formalin after the whole body contrast agent plus carrier agent (DMSO) perfusion while awaiting micro-CT scanning. As noted in the histology, the tunica intima differentially took up more stain than other components of the vessel and surrounding heart muscle. The tunica intima is seen as a bright white line on the innermost layer of the major vessel. This process allows one to clearly see the integrity of the vessel wall and presence of abnormalities using CT technology and without damaging the tissue. As an example, this process can be incredibly beneficial in studying vascular diseases such as atherosclerosis.

Example 14

Figure 14A:
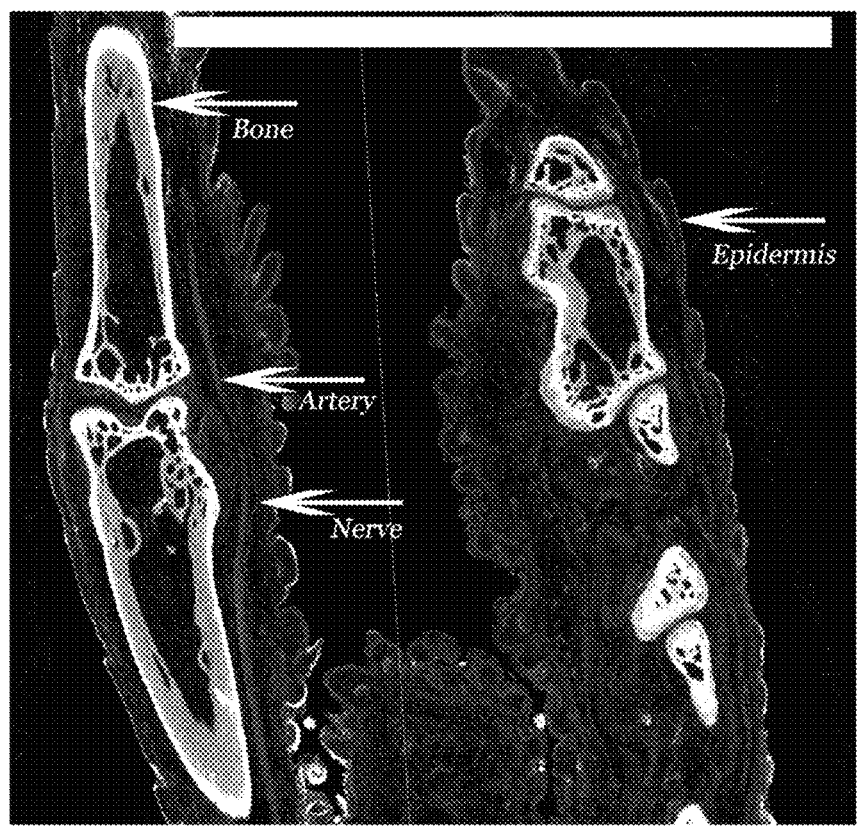
FIGS. 14A-14C illustrate differential staining of a pigeon foot at 4.5 µm resolution in accordance with embodiments of the present invention.
Figure 14B:
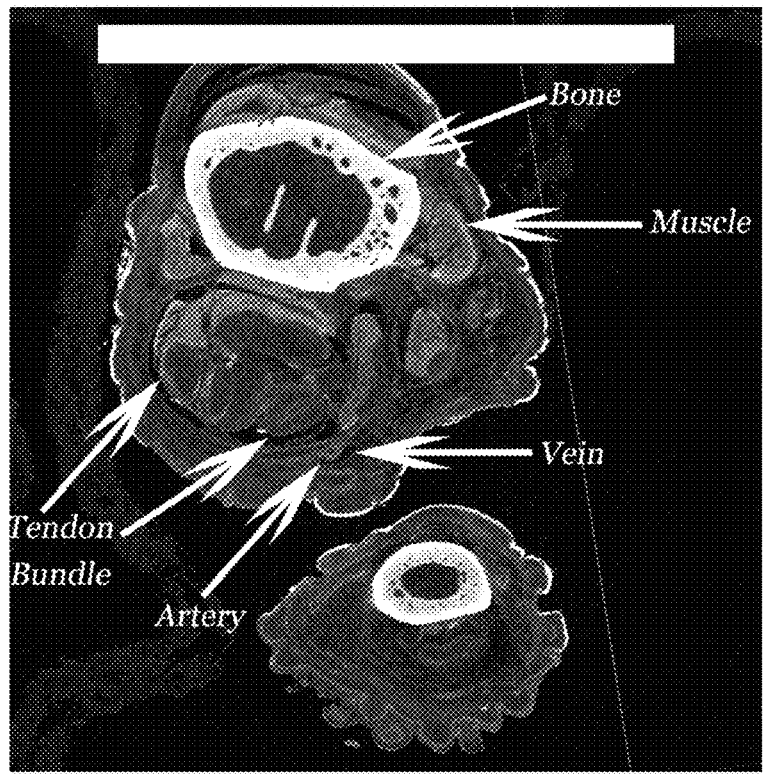
Figure 14C:
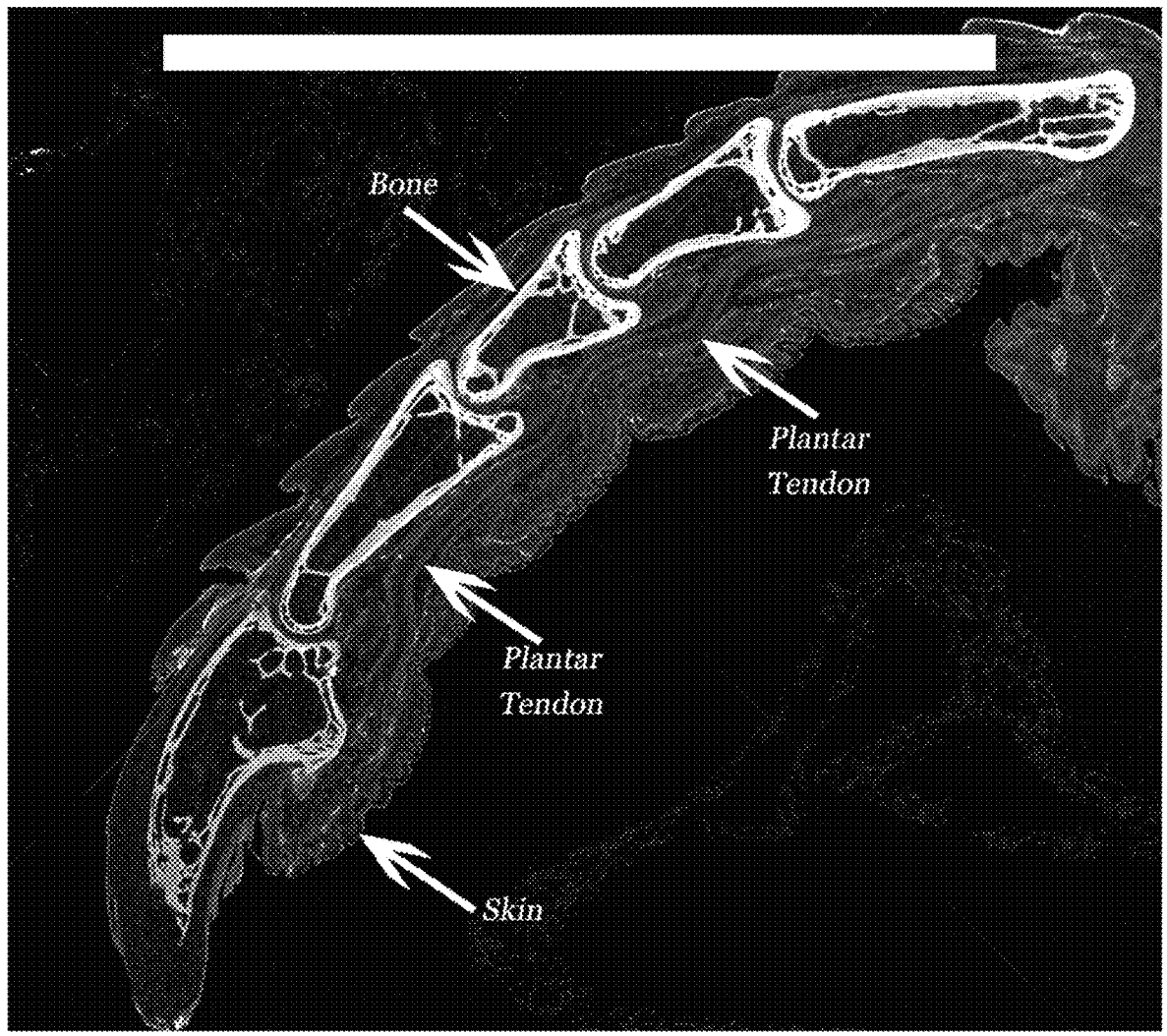

FIGS. 14A-14C show a pigeon foot perfused via local injections using a silver-based contrast agent plus a carrier agent (DMSO). The foot was CT scanned at 150 μm to demonstrate adequate distribution of radiodense particles and then stored in 10% formalin. Three months later, the foot was CT scanned at 4.5 μm resolution (shown here). In FIG. 14A, the thicker and more linear abaxial artery of digit 2 of the pigeon foot is shown adjacent to the thinner and more winding accompanying nerve in this coronal view of the toe. The bone and skin (epidermis) are also shown. This image demonstrates peripheral nerve staining visible via CT scanning previously not possible without the inventive imaging agent. FIG. 14B shows a cross-section of the contrast enhanced pigeon foot at 4.5 μm resolution near the proximal base of the two toes. The brighter (more dense) bone and muscle are contrasted against darker (less dense) individual tendons in a "tendon bundle" on the plantar surface of the digit. A smaller artery (with bright thick wall) is noted adjacent to a thinner-walled collapsed vein. Without contrast, the listed soft tissue structures are virtually indistinguishable from each other. The inventive imaging agent allows differential staining and significantly improved contrast as viewed with CT scanning. FIG. 14C shows a sagittal view and readily visible plantar tendon (running along the plantar surfaces of each phalanx), bones and skin (with epidermis, dermis and subcutaneous layers easily distinguishable). The inventive imaging agent again allows for even distribution of contrast and differential staining making soft tissue structures and their components easy to distinguish from one another.

Example 15

Figure 15A:
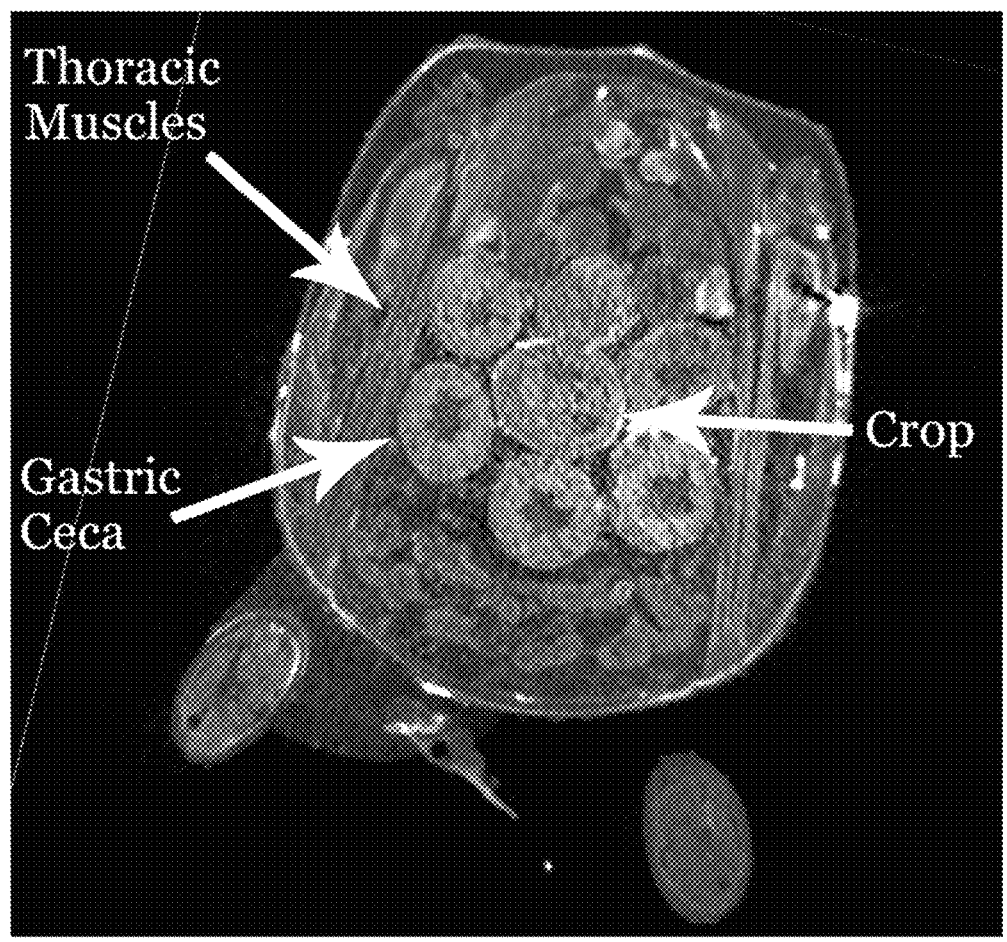
FIGS. 15A-15B illustrate staining of a grasshopper at 20 µm resolution in accordance with embodiments of the present invention.
Figure 15B:
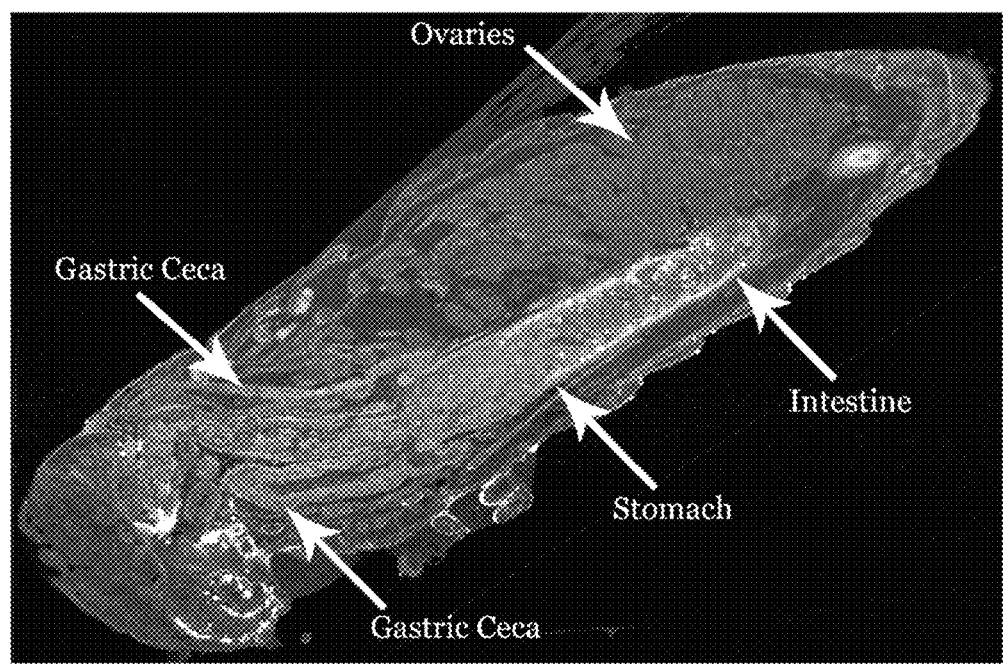

FIGS. 15A-15B show a female grasshopper perfused via abdominal injection using a silver-based contrast agent plus a carrier agent (DMSO). The grasshopper was scanned at 90 μm within two days of the perfusion to ensure good distribution of the agent. Then the animal was stored in 10% formalin and scanned one month later using micro-CT. FIG. 15A is a cross-section over the thorax region CT-scanned at 20 μm. The individual thoracic muscles are readily discernable from the gastric ceca (of which there are six) concentrically surrounding the circular crop. These structures are evenly and differentially stained making visualization easy. FIG. 15B shows a whole body sagittal section of the grasshopper scanned at 20 μm. Various organs are now readily visible that would otherwise not be distinguishable using CT. These images demonstrate how a single injection in the abdomen evenly diffused through the entire body for even staining of an insect.

Example 16

Figure 16A:
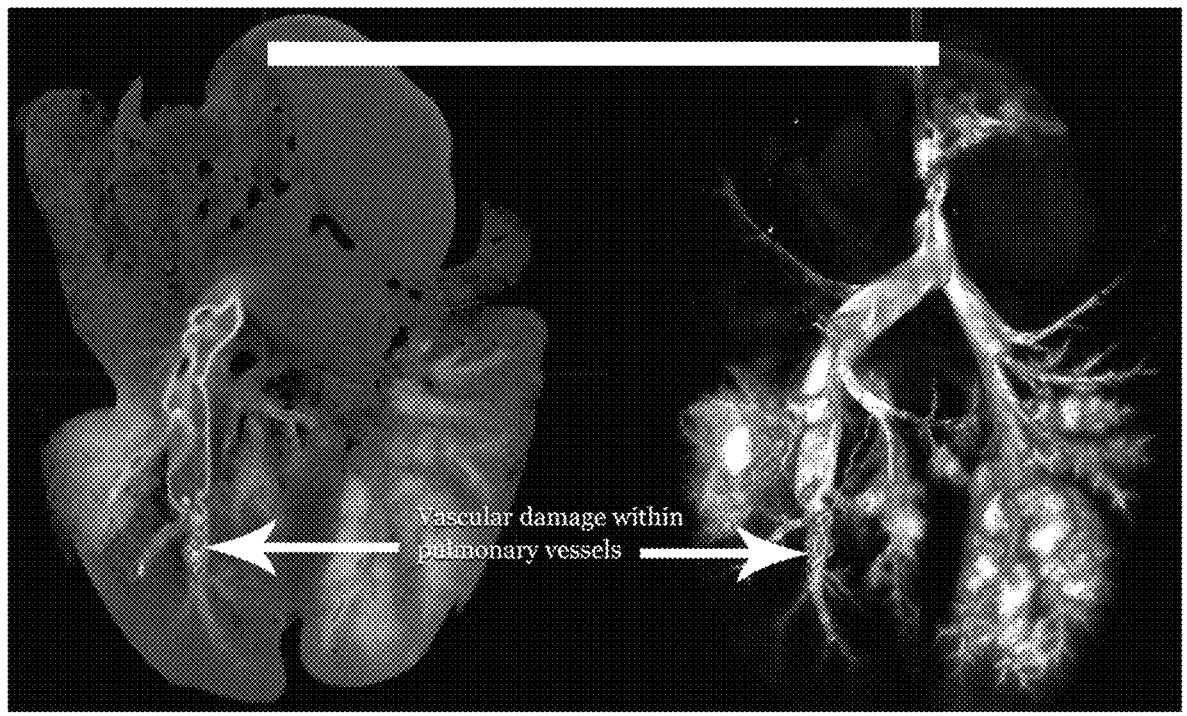
FIGS. 16A-16B illustrate staining of the lungs of a dog in accordance with embodiments of the present invention.
Figure 16B:
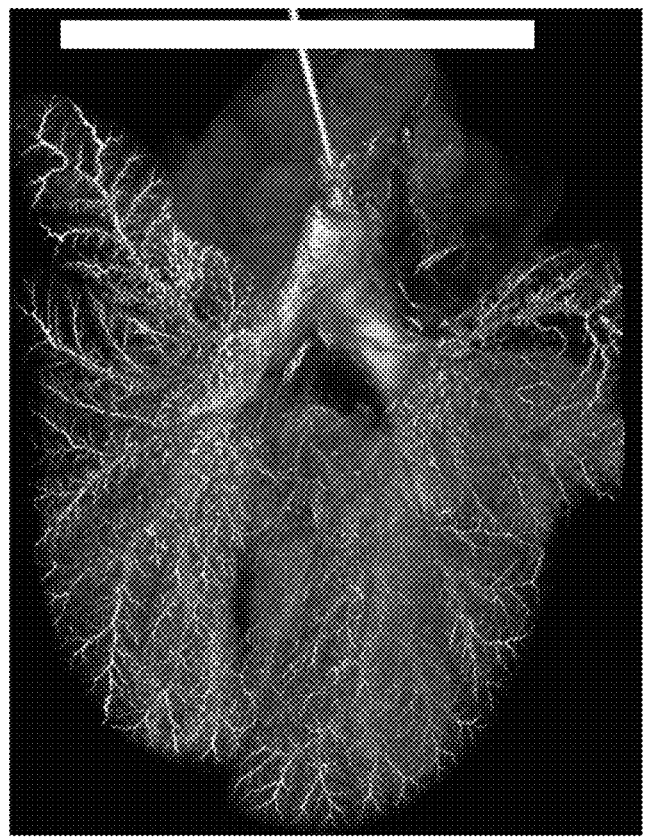

FIGS. 16A-16B show the lungs of a dog previously infected by heartworms and that later developed pulmonary vascular disease. The lungs were removed, vasculature flushed of blood and then preserved using a non-formaldehyde-based (glutaraldehyde and alcohol) fixative. Then the vasculature was fixed with an iodine-based contrast agent plus three carrier agents (DMSO, urea, ethanol) and two odor-reducing agents (orange and vanilla extracts). The lung was then CT-scanned at 200 μm slice thickness one hour after contrast staining with the inventive imaging agent. In FIG. 16A, the left image is a planar view while the right image is a volumetric reconstruction. The (left) planar view clearly shows the endothelial vascular damage represented by radiodense stippling, vascular wall thickening, and irregularity and vessel constriction. The (right) volumetric image shows irregularly shaped vessels. Additionally, both images show poor staining of the lung tissue towards the top of the image. FIG. 16B shows the same dog lungs cleared using alcohol and perfused using a sulfate-based non-diffusible contrast agent (BRITEVU®) injected into the vasculature (similar to the process depicted in FIG. 9C). The vasculature (as highlighted by the inventive imaging agent)

is far more extensive than stained soft tissue, but still abnormal compared to healthy lung vascular perfusions.

The two studies demonstrate several advantages of using this inventive imaging agent. First, the agent shows all tissue except the lumen of vessels (the opposite of the perfusible, non-diffusible agent that stays within the vasculature). This gives a completely different set of data points between the two methods and highlights different pathologies within the same tissue. For example, the inventive imaging agent highlights endothelial wall damage that is obscured by contrast agents that fill the vascular lumen and subsequently hides the pathology. Second, this combination of iodine-based contrast plus two carrier agents can be cleared using alcohol. This allows the vasculature to be later perfused with additional contrast agents. As a result, multiple studies can be performed on the same subject. Third, because the inventive imaging agents rapidly spread (diffuse), the CT can be collected within an hour or less of perfusion. This is simply not possible with previously reported means of diffusion staining.

Example 17

Figure 17:
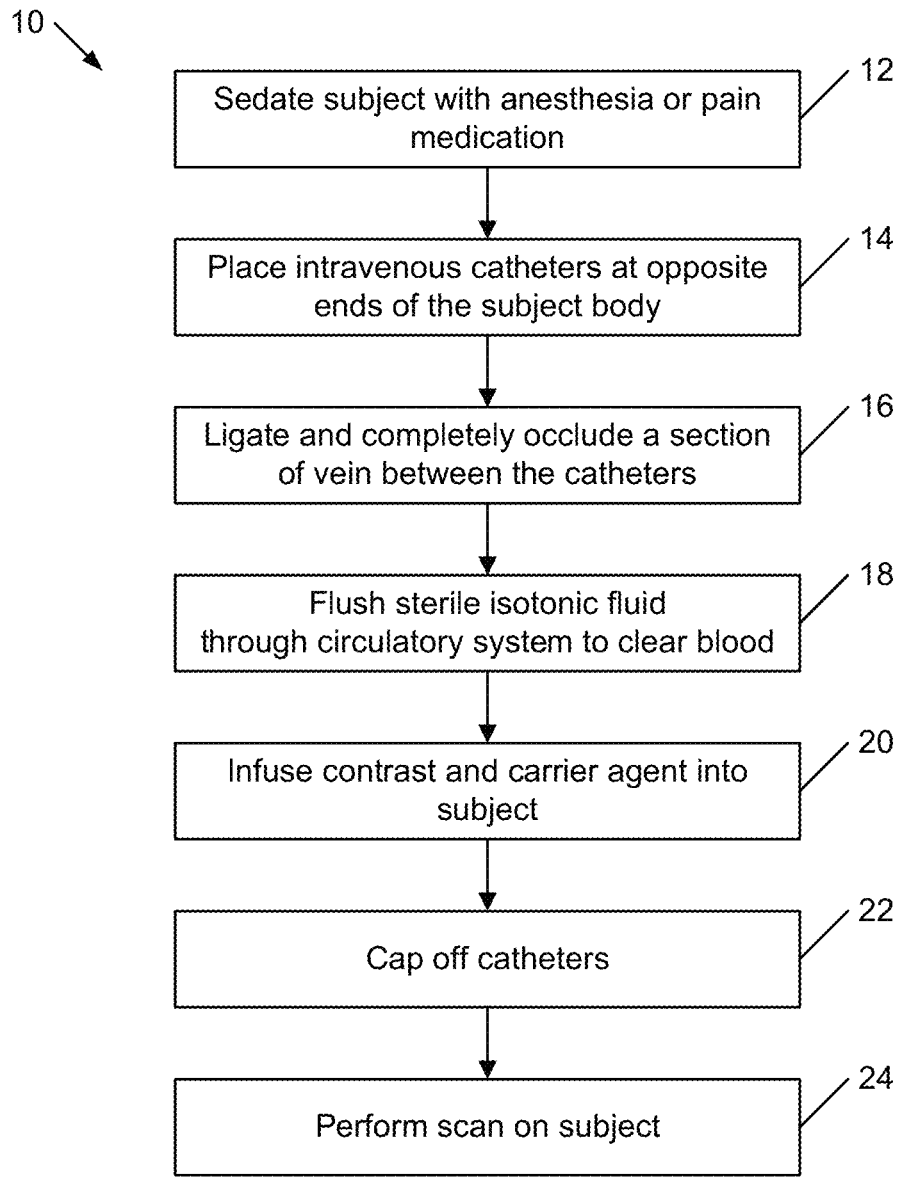
FIG. 17 is a flowchart of a process for introducing an embodiment of the inventive imaging agent to the cardiovascular system of a subject.

FIG. 17 is a flowchart of a process 10 for introducing an embodiment of the inventive imaging agent to the cardiovascular system of a subject. In operation 12, the subject is placed under anesthesia or heavily sedated with pain medication (alternatively, the subject may already be deceased). In operation 14, catheters or other entry means are placed at opposite ends of the subject's body. A "catheter" or entry means includes a catheter, a trocar, a cannula, a tube, or some other means of entering a subject's body. One, two, or more catheters may be placed at or near opposite ends of a chamber or system in the body of the subject. Such chamber may be a vein, an artery, a lymph vessel, a respiratory airspace, a cardiac space, an interstitial space, or other bodily chamber. Thus, the type of entry includes intravenous (IV), intraarterial (IA), intralymphatic (IL), intrarespiratory (IR), intracardiac (IC), intra-interstitial (II), or other intra-chamber or system (OIC). Ideally, one catheter carrying the inventive imaging agent is directed towards the heart (in the normal direction of venous flow), while the other catheter is directed away from the heart. However, both catheters can be placed towards the heart if needed. Alternatively, the same vein can be used with one catheter placed in the direction of the heart and one away from the heart. Alternatively, multiple catheters, trocars, tubes, etc. may be placed in multiple veins and/or arteries to deliver product to and drain blood components away from the subject. In operation 16, the section of vein between the two catheters is ligated and completely occluded. The two catheters must be securely sutured in place and around the vein to prevent leakage. Alternatively, one intravenous catheter can be placed, and a separate distant vein can be dissected from beneath the skin and either nicked (to allow for leakage) or ligated proximally (on the side towards the heart) and cut to allow drainage out the body.

Once the catheters are in place and with the subject completely anesthetized (or already deceased), in operation 18, a sterile fluid is flushed through the circulatory system to clear out the blood. The fluid may be sterile isotonic (normal body composition) fluids (such as 0.9% NaCl, 2.5% Dextrose, Lactated Ringer's Solution, NORMOSOL®, etc.), hypertonic (saturated saline solution, 7.5% saline solution, etc.) or hypotonic (distilled water, deionized water, etc.) and/or preservative fluids, with or without heparin (1:1000 U/ml) at 0.5-5 cc per 100 cc of selected fluids. The fluid is flushed in a catheter directed towards the heart (circulatory, lymphatic, respiratory or other system of the subject containing the vessel). Alternatively, the fluid may be flushed in catheters, trocars, and/or tubing that is directed away from the heart (for example, towards a distal extremity). While flushing the isotonic fluid, blood should come out the opposite IV (or IA or nick incision) site(s). Generally, 10-40% up to 300% of the subject's body weight worth of fluids is flushed. Regardless, enough isotonic, hypertonic, or hypotonic fluid should be introduced into the subject to produce clear to weak (Kool-Aid® consistency) blood-tinged fluid out the opposite IV, IA, or nick incision site(s). Optimal infusion pressures depend on the size and type of subject. Infusions may be hand delivered via a syringe or via an introducing machine. It is noted that an intraosseous (in the bone application of the mixture) catheter may also be used as a means to deliver the solution for skeletal imaging.

Once the blood has been adequately flushed from the body, in operation 20, the contrast and carrier agent (with or without other enhancing agents) mixture is infused into the IV or IA catheter(s) directed towards (or away from) the heart. The mixture is continually infused until it is exiting the opposite catheter(s) or nick site(s) as (visibly) concentrated as it is going in. Once the body has been judged adequately perfused, in operation 22, the catheter(s) is (are) capped or the nick site(s) is (are) lightly covered with a bandage to prevent further leakage. Optimal infusion pressures depend on the size and type of subject. Infusions may be hand delivered via a syringe or via an introducing machine.

In operation 24, the whole subject or harvested portions are then either stored (room temperature, cooled, in preservatives or fixatives depending on the time frame and purpose and plan of the study) or imaged using CT, MRI, photography and/or ultrasound. Imaging can begin immediately after infusion once all leakage has stopped. Harvested tissue can also be immediately scanned or soaked in standard fashion in formalin (or other preservative) for later scanning.

Besides the operations shown in FIG. 17, other operations or series of operations are contemplated to use the inventive imaging agent. For example, instead of the cardiovascular system of a subject, the process can be used to image the respiratory, lymphatic, or interstitial systems. Instead of a "vein" or "venous flow," the process may refer to a "vessel" or other chamber in the system and the flow through that chamber. Placement may be intravenous, intraarterial, intralymphatic, etc. In addition, before the scanning operation, the subject may be flushed or perfused with a radiopaque, non-diffusible contrast agent such as BRITEVU®. Moreover, the actual order of the operations in the flowchart in FIG. 17 is not intended to be limiting, and the operations may be performed in any practical order.

An imaging composition and methods for using the composition are provided that allow internal structures of a subject to be imaged more quickly, more uniformly, and more completely. Embodiments of the inventive composition may be used to perfuse whole subject systems to affect the entire subject, creating a density-staining process that can be completed in minutes to hours to days, compared to weeks or months previously. Previously diffusible contrast agents that diffused unevenly diffuse more evenly when combined with the carrier agent. Previously perfusible contrast agents that were not diffusible become diffusible when combined with the carrier agent.

The inventive composition may be composed of between 5% and 95% contrast agent and between 5% and 95% carrier agent. More preferably, the inventive composition may be composed of between 50% and 90% contrast agent and between 10% and 50% carrier agent. Odor-reducing and enhancing agents may comprise up to 5% of the total composition.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A composition for internal imaging of a subject, comprising:
    an imaging contrast agent; and
    at least one carrier agent that can pass through cellular and tissue membranes,
    wherein the composition can pass through cellular and tissue membranes.

2. The composition of claim 1, wherein the carrier agent comprises dimethyl sulfoxide, urea, or an alcohol.

3. The composition of claim 1, further comprising a second carrier agent.

4. The composition of claim 1, wherein the carrier agent comprises at least one of 1-dodecylazacycloheptan-2-one, a 2-N-nonyl-1,3-dioxolane, an N-acetyl prolinate ester, an alkyldiloxane, transcarbam, iminosulfurane, a capsaicin derivative, a cinnamene compound, a terpene, a chitosan nanoparticle, dimethyl sulfoxide, a hyaluronic acid-transethosome, an alcohol, and urea.

5. The composition of claim 1, wherein the imaging contrast agent comprises an iodine-based agent, a silver-based agent, or a barium-based agent.

6. The composition of claim 1, wherein the imaging contrast agent is radiodense.

7. The composition of claim 1, wherein the imaging contrast agent is perfusible.

8. The composition of claim 1, wherein the imaging contrast agent is diffusible.

9. The composition of claim 1, further comprising an enhancing agent.

10. The composition of claim 9, wherein the enhancing agent comprises a vasodilator or a vasoconstrictor.

11. The composition of claim 9, wherein the enhancing agent comprises epinephrine or atropine.

12. The composition of claim 9, wherein the enhancing agent is at least one of N-acetyl aspartate, choline, epinephrine, norepinephrine, an opioid, creatine, myosin, a cholinesterase compound, an anti-cholinesterase compound, a paralytic agent, a perfluorocarbon (PFC) based oxygen carrier, a lactate, a beta blocker, an antimicrobial, a calcium channel blocker, an antidepressant, an acetylcholinesterase inhibitor, a barbiturate, a non-opioid narcotic, a nonsteroidal anti-inflammatory agent, an enzyme, an enzyme inhibitor, or a target cell specific marker.

13. The composition of claim 1, further comprising an odor-reducing agent.

14. The composition of claim 13, wherein the odor-reducing agent comprises vanilla extract, orange extract, citrus extract, urea, or an alcohol.

15. The composition of claim 1, wherein the internal imaging comprises CT, X-ray, ultrasound, MRI, or photography.

16. The composition of claim 1, wherein the subject is a plant, a fungus, or an animal.

17. The composition of claim 1, wherein the subject is non-biologic.

18. A method for internally imaging a subject, comprising:
    placing a first entry means into a chamber or region of the subject at or near one or more ends of the subject's body;
    ligating a section of the chamber or region downstream and/or upstream from the first entry means;
    flushing fluid through a system of the subject being imaged to clear the contents of the system;
    infusing the subject with a composition comprising an imaging contrast agent and a carrier agent that can pass through cellular and tissue membranes, wherein the composition can pass through cellular and tissue membranes;
    capping off the first entry means; and
    scanning the subject.

19. The method of claim 18, wherein the first entry means comprises a catheter, trocar, cannula, or tube.

20. The method of claim 18, wherein a second entry means is placed at or near an opposite end of the subject's body from the first entry means.

21. The method of claim 18, wherein the chamber comprises a blood vessel, a lymphatic vessel, respiratory airspace, cardiac space, or interstitial space.

22. The method of claim 18, wherein the fluid comprises an isotonic, a hypertonic, a hypotonic, and/or a preservative fluid.

23. The method of claim 18, further comprising flushing or perfusing the subject with a radiopaque, non-diffusible contrast agent prior to scanning.

24. The composition of claim 1, wherein, in said infusing, the composition is composed of between 5% and 95% carrier agent.

25. The composition of claim 1, wherein the composition is composed of between 10% and 50% carrier agent.

26. The method of claim 18, wherein the composition is composed of between 5% and 95% carrier agent.

27. The method of claim 18, wherein, in said infusing, the composition is composed of between 10% and 50% carrier agent.

* * * * *